(12) United States Patent
Desai et al.

(10) Patent No.: US 11,850,384 B2
(45) Date of Patent: Dec. 26, 2023

(54) SYSTEMS AND METHODS FOR STEERING GUIDEWIRES

(71) Applicant: Georgia Tech Research Corporation, Atlanta, GA (US)

(72) Inventors: Jaydev P. Desai, Atlanta, GA (US); Yash Chetan Chitalia, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 884 days.

(21) Appl. No.: 16/491,680

(22) PCT Filed: Mar. 9, 2018

(86) PCT No.: PCT/US2018/021784
§ 371 (c)(1),
(2) Date: Sep. 6, 2019

(87) PCT Pub. No.: WO2018/165572
PCT Pub. Date: Sep. 13, 2018

(65) Prior Publication Data
US 2021/0128888 A1 May 6, 2021

Related U.S. Application Data

(60) Provisional application No. 62/469,570, filed on Mar. 10, 2017.

(51) Int. Cl.
*A61M 25/09* (2006.01)

(52) U.S. Cl.
CPC ............. *A61M 25/09041* (2013.01); *A61M 2025/09116* (2013.01); *A61M 2025/09141* (2013.01); *A61M 2205/0216* (2013.01)

(58) Field of Classification Search
CPC ...... A61M 25/09016; A61M 25/09025; A61M 25/09033; A61M 25/09041;
(Continued)

(56) References Cited

U.S. PATENT DOCUMENTS 5,916,147 A * 6/1999 Boury ............... A61M 25/0147
600/149
6,337,142 B2 * 1/2002 Harder ............... A61B 17/1631
428/596
(Continued)

FOREIGN PATENT DOCUMENTS

CN 105517502 A 4/2016
JP 4890463 3/2012
(Continued)

OTHER PUBLICATIONS

Office Action from application No. JP2016/214902 dated Nov. 30, 2021.
(Continued)

*Primary Examiner* — Tiffany Legette
*Assistant Examiner* — Leah J Swanson
(74) *Attorney, Agent, or Firm* — Troutman Pepper Hamilton Sanders LLP; Ryan A. Schneider; Ginger G. Turner

(57) ABSTRACT

Embodiments of the present disclosure can include a system for steering a guidewire comprising: a guidewire tip integrably connected to a guidewire, the guidewire tip comprising a hollow body having first joint and second joints comprising a plurality of asymmetric recesses in the hollow body; a plurality of tendons operably connected to the first and second joints; and a control unit operably connected to the tendons and configured to actuate the tendons to provide multiple degrees of freedom of movement to the guidewire tip.

22 Claims, 19 Drawing Sheets

(58) Field of Classification Search
CPC .......... A61M 25/0105; A61M 25/0147; A61M 25/0133; A61M 25/1038; A61M 2025/09116; A61M 2025/09175; A61M 2025/09183; A61M 25/0905; A61M 25/09; A61M 25/0136; A61M 25/0141; A61M 25/0144; A61M 25/01; A61M 2025/09133; A61M 2025/09125; A61M 2025/0063; A61M 2025/015; A61M 2025/0161; A61M 2025/0186; A61B 2034/301; A61B 2034/303; A61B 1/01; A61B 2017/00309; A61B 2017/00305; A61B 2017/00318; A61B 2017/00323; A61B 2017/00327

See application file for complete search history.

(56) References Cited

U.S. PATENT DOCUMENTS

| | | | |
|---|---|---|---|
| 10,363,398 B2 | 7/2019 | Gerrans | |
| 2004/0111044 A1* | 6/2004 | Davis | A61M 25/09016 600/585 |
| 2009/0192495 A1* | 7/2009 | Ostrovsky | A61M 25/0138 604/528 |
| 2016/0096004 A1 | 4/2016 | Gerrans | |
| 2016/0143633 A1* | 5/2016 | Robert | A61B 17/00234 604/95.04 |
| 2016/0346513 A1 | 12/2016 | Swaney et al. | |
| 2018/0042451 A1* | 2/2018 | Cuscuna | A61B 1/0011 |

FOREIGN PATENT DOCUMENTS

| | | |
|---|---|---|
| JP | 2016-214902 A | 12/2016 |
| WO | 2015/164912 | 11/2015 |

OTHER PUBLICATIONS

Search Report and Written Opinion from PCT application No. PCT/US18/21784 dated Jun. 14, 2018 (14 pages).

Extended European Search Report from application No. 18763256.7-1132 dated Dec. 17, 2020 (6 pages).

* cited by examiner

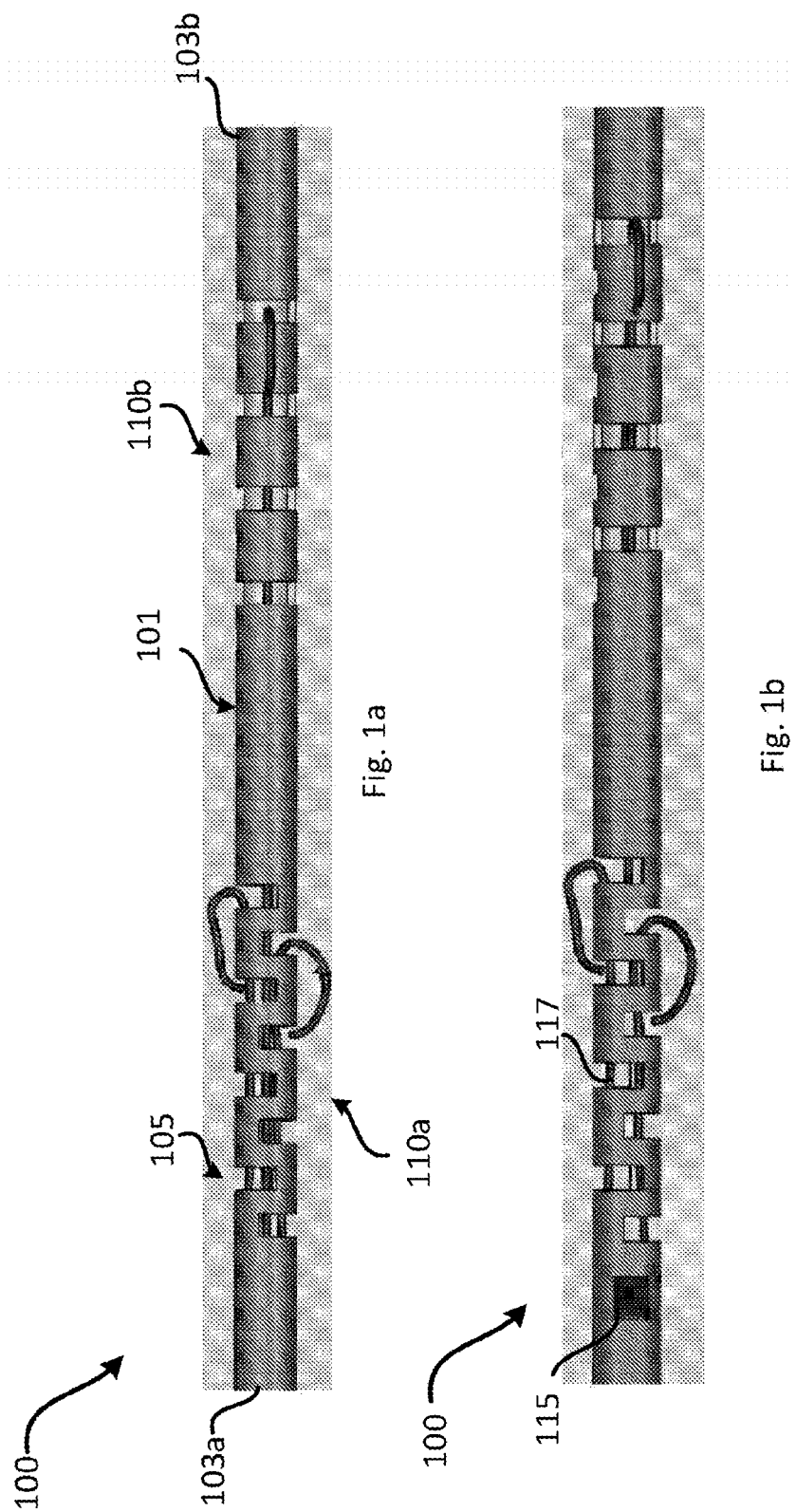

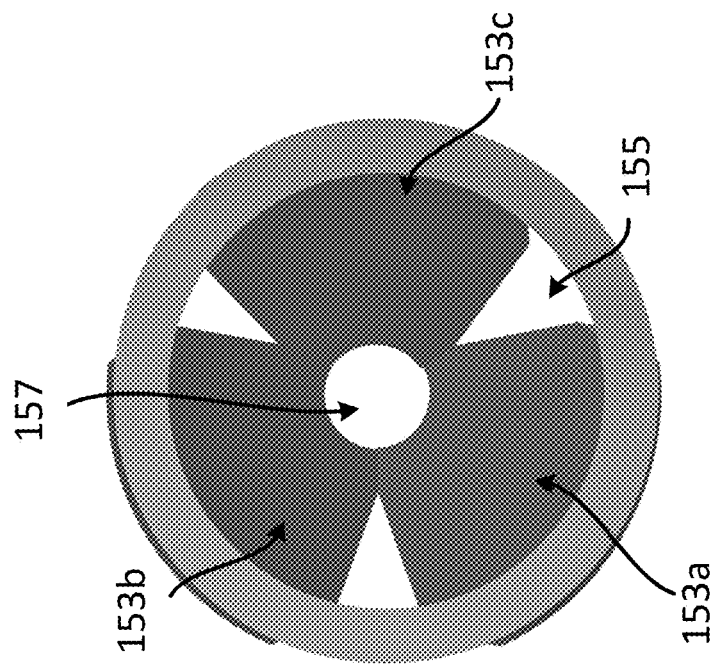
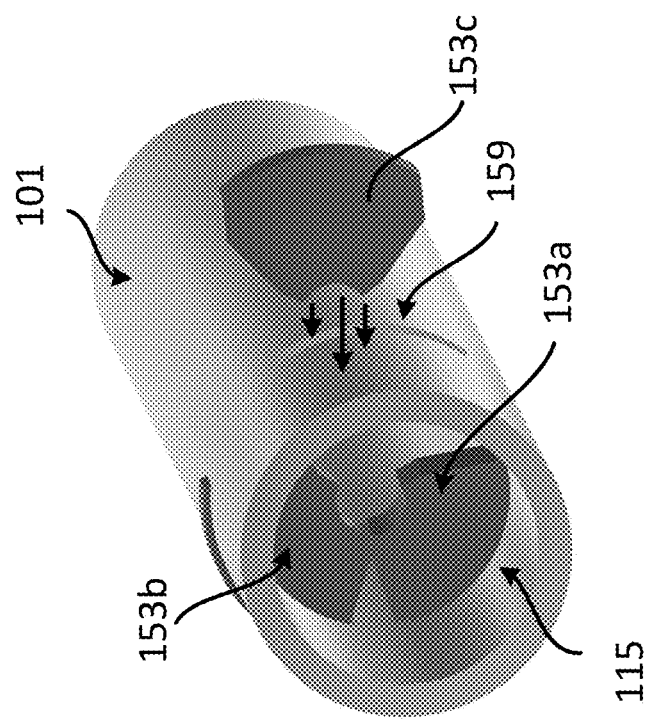

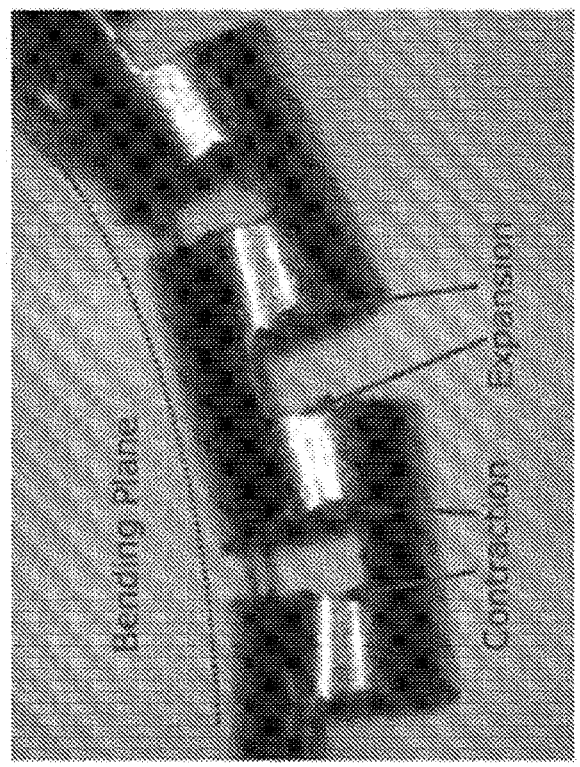
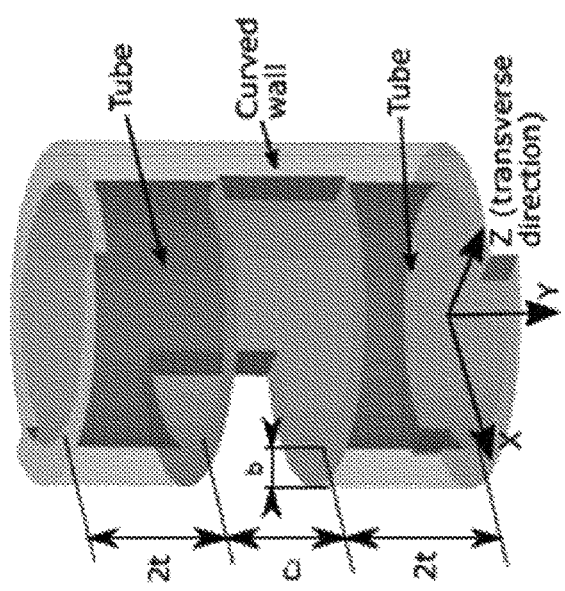
Fig. 8a
Fig. 8b

SYSTEMS AND METHODS FOR STEERING GUIDEWIRES

CROSS-REFERENCE TO RELATED APPLICATIONS

This application, filed 9 Mar. 2018, claims the benefit of U.S. Provisional Patent Application No. 62/469,570, filed 10 Mar. 2017, entitled "System, Method, and Apparatus for Active Control of Multiple Degrees-of-Freedom Micro-Scale Guidewires and Devices," the entire contents and substance of which are hereby incorporated by reference as if fully set forth below.

BACKGROUND

In most procedures for treating peripheral arterial disease (PAD), the operating surgeon must use a variety of catheters riding on a thin wire known as a guidewire. These catheters may be equipped with either the tools to perform the atherectomy, such as a micro-drill, or a drug delivery unit (in the form of a drug-coated balloon) to help prevent further deposition on that artery. The physician manually maneuvers the guidewire to the target artery by insertion, retraction, and rotation of the wire base, while observing its movement on a real-time fluoroscopic image. Such dexterous navigation of the guidewire tip under two-dimensional visual feedback is difficult and time consuming and requires significant experience.

BRIEF SUMMARY

The various embodiments of the present disclosure relate generally to systems and methods for steering guidewires.

Embodiments of the present disclosure can include a system for steering a guidewire, the system comprising: a guidewire tip integrably connected to a distal end of the guidewire, the guidewire tip comprising a hollow body having a first joint and a second joint, the first joint comprising a first plurality of asymmetric recesses in the hollow body and the second joint comprising a second plurality of asymmetric recesses in the hollow body; a first tendon, a second tendon, a third tendon, and a fourth tendon disposed within the hollow body of the guidewire tip, the first and second tendons operably connected to the first joint and the third and fourth tendons operably connected to the second joint; and a control unit operably connected to the first tendon and the second tendon, the control unit configured to actuate the first tendon and the second tendon to cause the first joint to bend in a manner providing a first degree of freedom of movement of the guidewire tip, the control unit further configured to actuate the third tendon and fourth tendon to cause the second joint to bend in a manner providing a second degree of freedom of movement of the guidewire tip different from the first degree of freedom of movement.

Embodiments of the present disclosure can include a guidewire tip for steering a guidewire, the guidewire tip comprising: a hollow elongated body including: a first joint comprising a first plurality of asymmetric recesses; and a second joint comprising a second plurality of asymmetric recesses; and a first tendon, second tendon, third tendon, and fourth tendon disposed within the hollow elongated body, the first tendon and second tendon operably connected to the first joint, and the third tendon and fourth tendon operably connected to the second joint.

In any of the above embodiments, the first joint and the second joint can be co-located.

In any of the above embodiments, the first joint and the second joint can be separated by a first length.

In any of the above embodiments, the hollow body can comprise a first end and an opposing second end, and wherein the first joint is separated from the second end by a second length.

In any of the above embodiments, the guidewire tip can have a width from about 0.1 mm to about 0.9 mm.

In any of the above embodiments, the hollow body can comprise an internal wall, the first tendon and the second tendon can be disposed on opposing sides of the internal wall, and the third tendon and fourth tendon can be disposed on opposing sides of the internal wall.

In any of the above embodiments, the first, second, third, and fourth tendons can comprise a superelastic wire.

In any of the above embodiments, the first tendon and second tendon can be attached to a distal end of the first joint and the third tendon and fourth tendon can be attached to a distal end of the second joint.

In any of the above embodiments, each recess in the first and second pluralities of recesses can be one of rectangular, triangular, or sinusoidal in shape.

In any of the above embodiments, the guidewire tip can be composed of a biocompatible material. For instance, in any of the above embodiments, the guidewire tip can be composed of nitinol.

In any of the above embodiments, the system can further comprise a routing wedge disposed within the hollow body proximate a base of the hollow body, the routing wedge spatially separating the first and second tendons, and the routing wedge spatially separating the third and fourth tendons. In some embodiments, the routing wedge can comprise a plurality of wedge portions, and the plurality of wedge portions can define a central channel and a plurality of outer channels. In some embodiments, the system can further comprise a plurality of slots disposed within the hollow elongated tube and for receiving the plurality of wedge portions.

In any of the above embodiments, the control unit comprises a guidewire actuation assembly and a guidewire roller mechanism. In some embodiments, the guidewire actuation assembly can comprise a plurality of motors for advancing, retracting, and rotating the guidewire. In some embodiments, the guidewire actuation assembly can comprise a first motor for advancing the guidewire through the guidewire roller mechanism. In some embodiments, the guidewire roller mechanism can comprise a first roller and a second roller, the guidewire roller mechanism operably coupled to a first motor, and a portion of the guidewire can be disposed between the first and second rollers. In any of the above-described embodiments, the control unit can further comprise a groove path for storing the guidewire. In any of the above-described embodiments, the control unit can further comprise a shaft operably coupled to an elastic coupling, the shaft can be operable by a second motor and configured to unspool the guidewire from the groove path to the guidewire roller mechanism.

In any of the above embodiments, the first plurality of asymmetric recesses can be orthogonal to the second plurality of asymmetric recesses. In any of the above embodiments, the guidewire tip and the guidewire can be a continuous body.

BRIEF DESCRIPTION OF THE DRAWINGS

FIGS. 1a-1c show schematics of a guidewire tip having a two-dimensional asymmetric recess design, in accordance with an exemplary embodiment of the present disclosure.

FIGS. 1*d* and 1*e* show a schematic and cross-sectional view, respectively, of a routing wedge, in accordance with an exemplary embodiment of the present disclosure.

FIGS. 8*a* and 8*b* are a schematic modeling a single recess in the joint as a combination of two tubes and a curved wall and an image showing deformation of recess when it is bending, respectively, and in accordance with an exemplary embodiment of the present disclosure.

DETAILED DESCRIPTION

Figure 1C:
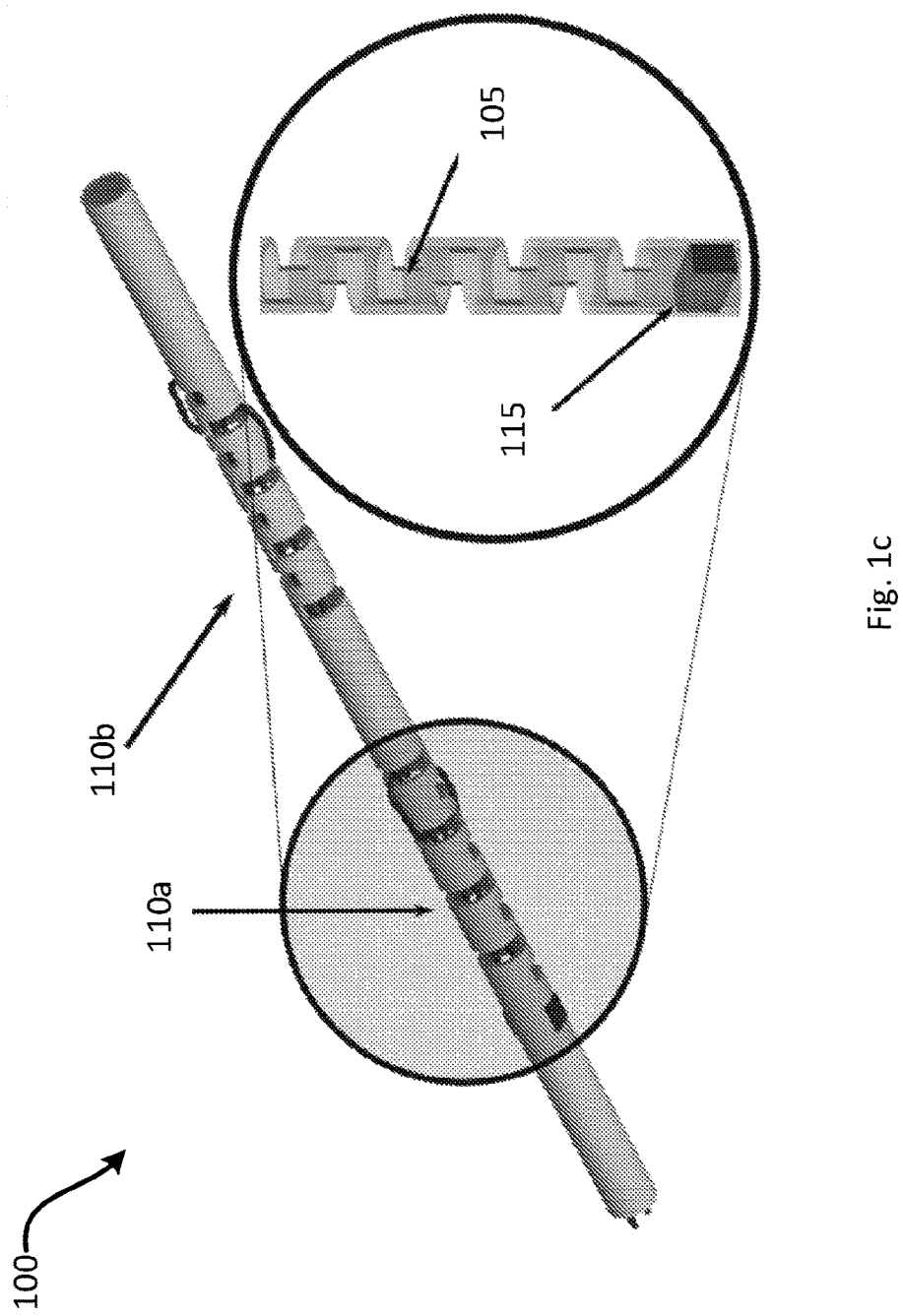

Although preferred embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. The disclosure is capable of other embodiments and of being practiced or carried out in various ways. Also, in describing the preferred embodiments, specific terminology will be resorted to for the sake of clarity.

It must also be noted that, as used in the specification and the appended claims, the singular forms "a," "an" and "the" include plural referents unless the context clearly dictates otherwise.

Also, in describing the preferred embodiments, terminology will be resorted to for the sake of clarity. It is intended that each term contemplates its broadest meaning as understood by those skilled in the art and includes all technical equivalents which operate in a similar manner to accomplish a similar purpose.

Ranges can be expressed herein as from "about" or "approximately" one particular value and/or to "about" or "approximately" another particular value. When such a range is expressed, another embodiment includes from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

Embodiments of the present disclosure relate to guidewire steering systems and guidewire tips that can offer multi-degrees of freedom of movement to the guidewire tip. In an exemplary embodiment, the present disclosure includes guidewire tips comprising, for example, two orthogonally-oriented joints comprising a plurality of asymmetric recesses that offer two degrees-of-freedom to the guidewire tip. Known guidewires must be manually maneuvered through a target artery by insertion, retraction, and rotation of the wire base, while observing its movement on a real-time fluoroscopic image. Such dexterous navigation of the guidewire tip under two-dimensional visual feedback is difficult and time consuming and requires significant experience. The presently disclosed embodiments can be advantageous because they expand the workspace of the guidewire and provide a physician with the ability to navigate at the distal end of the guidewire to go around plaque or other structures, such as a vessel bifurcation along the path. In other words, embodiments of the present disclosure can allow a physician to steer the guidewire through acute arterial routes.

Further advantages of the presently disclosed embodiments can include that a physician can teleoperatively control guidewire motion without exposing themselves to radiation or the patient to excessive radiation doses. This control of the guidewire system can be facilitated with the use of a joystick interface. In this system, the physician can continuously control the degree of insertion of the guidewire in the blood vessel based on for example, fluoroscopy images, a rotation of the guidewire/torque the wire, if necessary, and actuating the distal degrees of freedom. The location of the tip of the guidewire can be determined by the insertion length of the guidewire in the vessel as well as the actuation of the distal degrees of freedom. The system can be extremely flexible, since it can enable the physician to control all aspects of the procedure. The presently disclosed embodiments can be particularly useful for treatment of peripheral arterial disease (PAD) using a atherectomy procedure, which requires the guidewire to be in place before it is done.

FIGS. 1a-1c show exemplary guidewire tips 100, in accordance with one or more embodiments of the present disclosure. As shown in FIGS. 1a and 1b, the guidewire tips 100 can comprise a hollow, elongated body 101 having a first end 103a and a second end 103b and including two or more joints 110a, 110b. As illustrated at FIG. 1c, the two or more joints 110a, 110b can include a plurality of recesses 105. In some embodiments, the hollow, elongated body 101 can include a first joint 110a comprising a first plurality of recesses 105 and a second joint 110b comprising a second plurality of recesses. In some embodiments, the plurality of recesses 105 can allow for multiple degree-of-freedom movement of the guidewire tip 100.

Figure 2A:
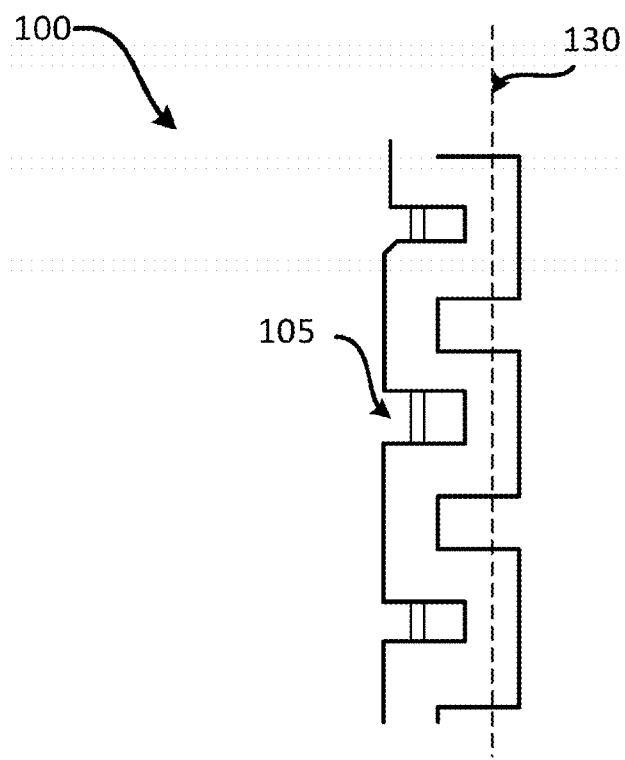
FIG. 2*a* shows a schematic of an asymmetric recess design, in accordance with an exemplary embodiment of the present disclosure.

In some embodiments, the hollow, elongated body can be a tube. In some embodiments, some or all of the recesses can be asymmetric recesses, as illustrated in FIG. 2a. Recesses that are asymmetric can be described as recesses that can cause the neutral bending plane 130 of the device to be offset towards an outer edge of the device as opposed to down a central axis of the device, which is generally seen with symmetric recesses. An asymmetric pattern of recesses can allow the guidewire tip to be bent with a longer moment arm in one direction in the plane of the recess cut, thus allowing a larger range of motion.

In some embodiments, the first plurality of recesses can be orthogonal to the second plurality of recesses, as illustrated in FIGS. 1a-1c. This can allow the first and second joints to be orthogonal to one another. Orthogonality of the joints can be achieved by rotating the hollow elongated body by 90 degrees with respect to the first plurality of recesses and machining the second plurality of recesses. In other embodiments, the first plurality of recesses need not be orthogonal to one another. For instance, the second plurality of recesses can be offset from the first plurality of recesses by 5 degrees, 10 degrees, 15 degrees, 20 degrees, 35 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 95 degrees, 100 degrees, 105 degrees, 110 degrees, 115 degrees, 120 degrees, 125 degrees, 130 degrees, 135 degrees, 140 degrees, 145 degrees, 150 degrees, 155 degrees, 160 degrees, 165 degrees, 170 degrees, 175 degrees, or 180 degrees. In some embodiments, the second plurality of recess can be offset from the first plurality of recess by from 1 to 5 degrees, from 6 to 10 degrees, from 11 to 15 degrees, from 16 to 20 degrees, from 21 to 25 degrees, from 26 to 30 degrees, from 30 to 45 degrees, from 45 to 60 degrees, from 60 to 75 degrees, from 75 to 90 degrees, from 90 to 100 degrees, from 100 to 120 degrees, from 120 to 135 degrees, from 135 to 150 degrees, from 150 to 160 degrees, from 160 to 175 degrees, or from 175 to 180 degrees.

The individual recesses making up each plurality of recesses can be any geometric shape. In an exemplary embodiment, the recesses can be rectangular. In other embodiments, the recesses can be, for example, sinusoidal or triangular-shaped. In some embodiments, the plurality of recesses can be different shapes. In other embodiments, the first joint can have a first plurality of recesses that has a different shape from the second plurality of recesses. In an embodiment, the shape of the recesses can be selected from the group consisting of rectangular, sinusoidal, semi-circular, or triangular.

Figure 2B:
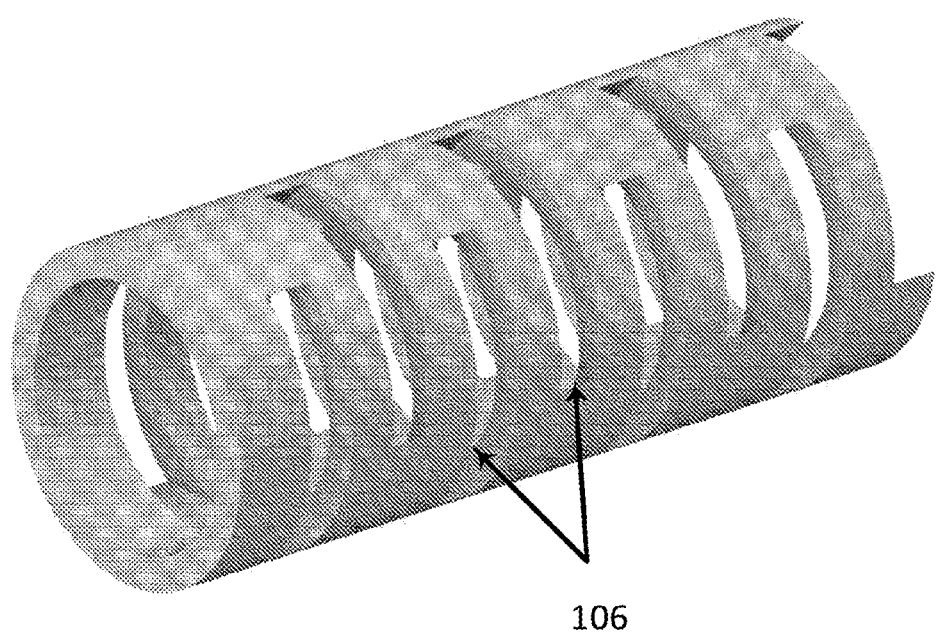
FIG. 2*b* shows a schematic of an asymmetric recess design with co-located degrees of freedom, in accordance with an exemplary embodiment of the present disclosure.

The guidewire tip can be defined by a width and a length. The recesses can be defined by a depth. In some embodiments, the depth of the recesses can be greater than 50% of the width of the guidewire tip. In some embodiments, the depth of the recesses can be about 55%, about 60%, about 65%, about 70%, about 75%, about 80%, about 85%, about 90%, or about 95% the width of the guidewire tip. In some embodiments, the depth of the recesses can be from about 51% to about 54%, about 56% to about 59%, about 61% to about 64%, about 66% to about 69%, about 71% to about 74%, about 76% to about 79%, about 81% to about 84%, about 86% to about 89%, or about 91% to about 94% the width of the guidewire tip. In other embodiments, the depth of the recesses can be 50% or less of the width of the guidewire tip. For instance, in some embodiments, the depth of the recesses can be about 10%, about 15%, about 20%, about 25%, about 30%, about 35%, about 40%, about 45%, or about 50% the width of the guidewire tip. In some embodiments, the depth of the recesses can be from about 11% to about 14%, about 16% to about 19%, about 21% to about 24%, about 26% to about 29%, about 31% to about 34%, about 36% to about 39%, about 41% to about 44%, or about 46% to about 49% the width of the guidewire tip. Indeed, in some embodiments, not every recess in the plurality of recesses need have the same depth such that the depth can vary between the recesses. In an embodiment shown in FIG. 2b, recesses 106 can allow co-located but non-orthogonal two degree of freedom movement. Recesses 106 can be designed not to exceed 50% of the width of the hollow elongated body. In other embodiments, the recesses can be co-located and can exceed 50% of the width of the hollow elongated body. In embodiments with co-located recesses, the recesses can be about 25% of the circumferences of the hollow elongated body. In an embodiment with co-located recesses, the joint can move in both degrees-of-freedom due to the recesses being in the same location.

The guidewire tip can have multi-degree of freedom movement. For instance, in some embodiments, such as those illustrated in FIGS. 1a-1c, the guidewire tip can have two degrees of freedom. However, it is contemplated that the embodiments of the present disclosure can include more than two degrees of freedom of movement. This can be achieved by adjusting the number and orientation of the joints along the hollow, elongated body. For instance, additional degrees of freedom may be included by creating more joints comprising additional pluralities of asymmetric recesses at a location where the additional degree of freedom is desired.

In some embodiments, the first and second joints can be separated by a first length. For instance, in some embodiments, the first length can include any length up until about the entire length of the guidewire. For instance, in some embodiments, the second joint can be co-located with the first joint (as illustrated, e.g., in FIG. 2b) such that the second joint immediately follows the first joint such that the distance between the first and second joints is not greater than the distance between individual recesses. In other embodiments, the first and second joints can be separated by a first length of a predetermined length depending on the desired location of the degrees of freedom along the guidewire.

The hollow body can comprise a first end and an opposing second end. In some embodiments, the first joint can be separated from the first or second end by a second length. In some embodiments, the second length can be adjusted such that the first joint begins at or near the first end of the guidewire tip. The length between the first joint and the first or second end can be adjusted as desired depending on the desired location of the degrees of freedom along the guidewire.

It is noted that while an exemplary embodiment of the present disclosure can be a system for steering a guidewire through an artery, other applications of the invention are contemplated, such as, for example, use in endoscopic tools, maneuverable endoscopic tools for neurosurgery, ophthalmology or urology, or any such application where miniature endoscopic tools may be used. In other words, by use of the term "guidewire" throughout it is understood that "guidewire" can refer to other tools allowing maneuvering through a portion of a body.

In some embodiments, for example, where the guidewire is used through an artery, the guidewire tip can have a width of from about 0.1 mm to about 0.9 mm. In some embodiments, the width of the guidewire tip can be about 0.3, 0.33 mm, about 0.35 mm, about 0.4 mm, about 0.45 mm, about 0.50 mm, about 0.55 mm, about 0.60 mm, about 0.65 mm, about 0.7 mm, about 0.75 mm, about 0.78 mm, about 0.8 mm, about 0.85 mm, about 0.88, or about 0.89mm about 0.9 mm. In some embodiments the width of the guidewire can be from about 0.31 mm to about 0.34 mm, about 0.36 mm to about 0.39 mm, about 0.41 mm to about 0.44 mm, about 0.46 mm to about 0.49 mm, about 0.51 mm to about 0.54 mm, about 0.56 mm to about 0.59 mm, about 0.61 mm to about 0.64 mm, about 0.66 mm to about 0.69 mm, about 0.71 mm to about 0.74 mm, about 0.76mm to about 0.79mm, about 0.81 mm to about 0.84 mm, or about 0.86 mm to about 0.89 mm. In an embodiment, the guidewire tip can have a width of greater than about 1.0 mm. For example, in pediatric neurosurgeries, endoscopic tools with a width of about 2.0 mm can be used.

In some embodiments, a plurality of tendons can be disposed within the hollow, elongated body. In an exemplary embodiment, a first tendon, a second tendon, a third tendon, and a fourth tendon can be disposed within the hollow elongated body, as illustrated at FIGS. 1a and 1b. In some embodiments, the first and second tendons can be operably connected to the first joint and the third and fourth tendons can be operably connected to the second joint. In some embodiments the first and second tendons can be operably connected to the distal end of the first joint and the third and fourth tendons can be operably connected to the distal end of the second joint. In some embodiments, the plurality of tendons can be soldered to a distal end of the joints. In other embodiments, an interior wall of the hollow-elongated body can comprise a plurality of slits that can hold the tendons parallel to the wall and in which the tendons can terminate. The tendons can be operably connected to a particular interior wall of the hollow-elongated body. For example, in an embodiment, the first tendon can be operably connected to a first interior wall of the first joint and the second tendon can be operably connected to a second interior wall of the first joint. In an embodiment, the third tendon can be operably connected to a first interior wall of the second joint and the fourth tendon can be operably connected to a second interior wall of the second joint.

In some embodiments, the plurality of tendons can be composed of superelastic wires. A superelastic material may include any material that can deform reversibly to strains of up to about 10%. For instance, in some embodiments, the tendons can be composed of Nitinol. However, it is understood that the tendons can be composed of any biocompatible material, including biocompatible materials that are not necessarily superelastic, including but not limited to biocompatible metals, biocompatible alloys, biocompatible plastics, or materials comprising biocompatible coatings, and the like. Other biocompatible materials may include, for example and not limited to, titanium, or stainless steel, and the like.

Further, in some embodiments, as illustrated at FIG. 1a-1e, the guidewire tip can further comprise one or more routing wedges 115 disposed within the hollow body proximate a distal end of the hollow body. The one or more routing wedges can be used for spatially separating the plurality of tendons 117. For instance, as illustrated at FIGS. 1a-1e, the routing wedges 115 can comprise a plurality of wedge portions 153a, 153b, 153c disposed about a central channel 157. The central channel 157 can be used for controlling tendons 117 and other hardware through the interior of the hollow elongated body 101. Additionally, as illustrated at FIG. 1d-1e the plurality of wedge portions 153a, 153b, 153c can each be separated by an outer channel 155 for routing tendons 117 and other hardware within the interior of the hollow elongated body. In some embodiments, the plurality of wedge portions 153a, 153b, 153c can be composed of an elastic material to provide stiffness gradation. In some embodiments, the plurality of wedge portions 153a, 153b, 153c can be 3-D printed and inserted independently into the hollow elongated body 101 through slots 159 cut into the hollow elongated body. In some embodiments, the slots 159 can be laser-cut. As will be understood, once all the wedges 153a, 153b, 153c are inserted within the hollow elongated body 101, the central 157 and outer channels 155 are formed.

When integrated with a system for steering a guidewire, the tendons can be actuated to cause the joints to bend in a manner providing a degree of freedom. For example, the first and the second tendons can be actuated to cause the first joint to bend in a manner providing a first degree of freedom of movement of the guidewire tip and the third and fourth tendons can cause the second joint to bend in a manner providing a second degree of freedom of movement of the guidewire tip. In some embodiments, the first degree of freedom can be different from the second degree of freedom. In some embodiments, the plurality of tendons can permit the joints to be controlled bi-directionally.

The hollow elongated body can comprise an internal wall. In some embodiments for providing two degree of freedom movement, the first tendon and the second tendon are disposed on opposing sides of the internal wall, and the third tendon and fourth tendon are disposed on opposing sides of the internal wall. In some embodiments, the first, second, third, and fourth tendons can be disposed at different locations. In an embodiment, additional degrees of freedom can be provided by operably connecting additional tendons to additional joints on the hollow-elongated body. In some embodiments, the tendons can be routed through the hollow, elongated body about a central-most portion and bifurcate where needed to attach to the hollow elongated body.

The guidewire and the guidewire tip can be composed of any biocompatible material. In some embodiments, the biocompatible material is a biocompatible metal or alloy. In some embodiments, the biocompatible material is nitinol. For instance, in some embodiments, one or both of the guidewire and guidewire tip can be composed of Nitinol. However, it is understood that the guidewire and guidewire tip can be composed of any biocompatible material that can handle high strains without deformation, including biocompatible materials that are not necessarily superelastic, including but not limited to biocompatible metals, biocompatible alloys, biocompatible plastics, or materials comprising biocompatible coatings. Other biocompatible materials may include, for example and not limited to, titanium, or stainless steel.

The guidewire tips and respective recesses can be manufactured using any known process and machinery capable of micro-machining. For instance, in some embodiments, the respective recesses can be manufactured using a femtosecond laser, picosecond laser, or a nanosecond laser. The lasers can be of varying wavelengths and include, for instance, an infrared laser. A micro-mill may also be used for the same purpose, for guidewires of larger widths.

Embodiments of the present disclosure can include a system for steering a guidewire through an artery, the system comprising a guidewire tip integrably connected to a distal end of the guidewire, the guidewire tip comprising a hollow body having a first joint and a second joint, the first joint comprising a first plurality of asymmetric recesses in the hollow body and the second joint comprising a second plurality of asymmetric recesses in the hollow body; a first tendon, a second tendon, a third tendon, and a fourth tendon disposed within the hollow body of the guidewire tip, the first and second tendons operably connected to the first joint and the third and fourth tendons operably connected to the second joint; and a control unit operably connected to the first tendon and the second tendon, the control unit configured to actuate the first tendon and the second tendon to cause the first joint to bend in a manner providing a first degree of freedom of movement of the guidewire tip, the control unit further configured to actuate the third tendon and fourth tendon to cause the second joint to bend in a manner providing a second degree of freedom of movement of the guidewire tip different from the first degree of freedom of movement.

The guidewire tip can be integrably connected with a guidewire. For instance, in some embodiments the guidewire tip can be the tip of the guidewire itself and not a separate piece. In other words, the guidewire tip and the guidewire can be a continuous body. In other embodiments, the guidewire tip can be a separate piece that may be micro-welded or press-fit on the body of the guidewire or micro-machined after encapsulating the tip.

Figure 3A:
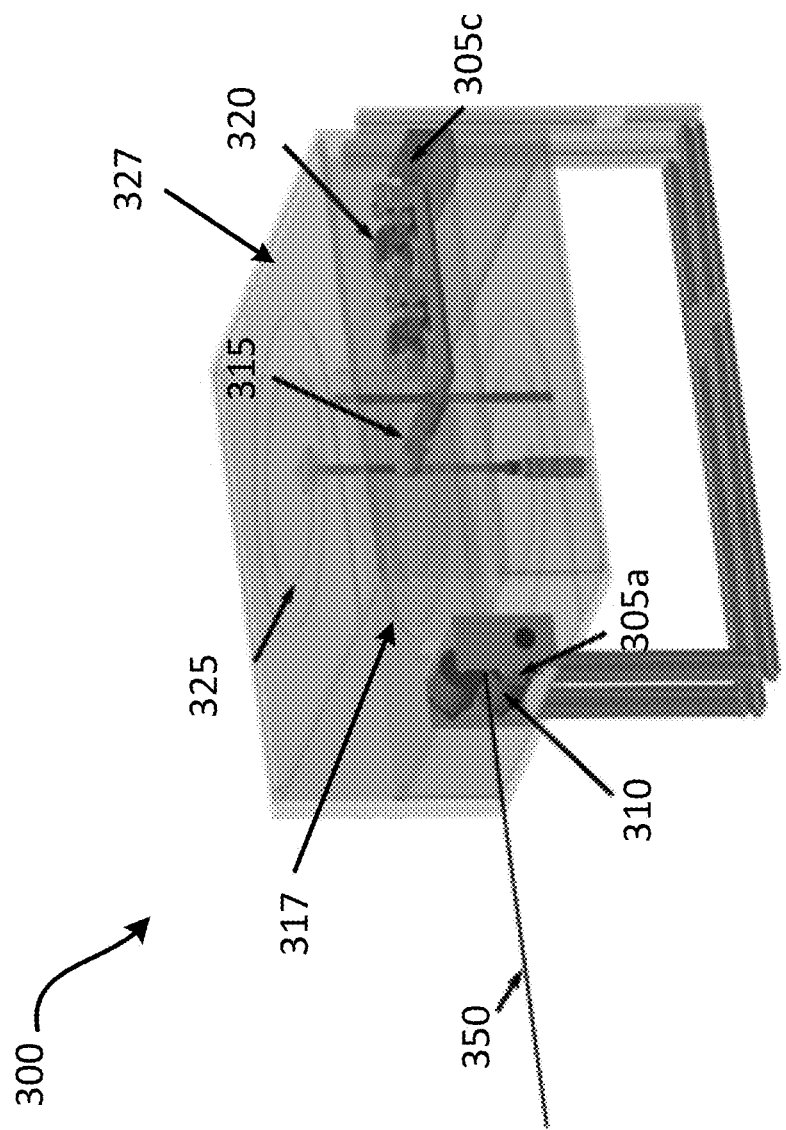
FIG. 3*a*-3*c* show schematics of a control unit for guidewire actuation and advancement, in accordance with an exemplary embodiment of the present disclosure.

In some embodiments, the system for steering a guidewire through an artery can comprise a control unit operably connected to the plurality of tendons and the guidewire. The control unit can be used for, e.g., actuation and advancement of the guidewire through the artery. In some embodiments, the system for steering the guidewire can be automated and comprise four degrees-of-freedom to enable: 1) distal two degree of freedom bending capability of the guidewire, 2) the ability to advance and retract the guidewire from the vasculature with the aid of motion from a plurality of motors, 3) rotation of the guidewire inside the vasculature with the aid of the plurality of motors. To enable distal dexterity, motors can be used (such as a piezomotor, for example) to enable pitch and yaw motion capability. By enabling dexterity in the guidewire along the length (primarily in the last 5 mm of the distal section), distal steering capability of the guidewire can be enabled FIG. 3a shows an exemplary control unit 300 enabling four degrees of freedom of movement. To enable rotation of the guidewire inside the blood vessel, the entire guidewire actuation assembly can be mounted on a shaft and the motion of that shaft can be controlled by motor 305b. Furthermore, to advance and retract the guidewire 350 from the blood vessel, the motor 305b can be attached to a shaft with elastic coupling 315 to enable moving the guidewire actuation assembly 320 inside a spiral groove 325 of a guidewire track 327. The guidewire track can be an enclosure alongside and parallel to the spiral groove 325 where the entire guidewire actuation assembly can move to control the guidewire degrees of freedom.

Figure 3B:
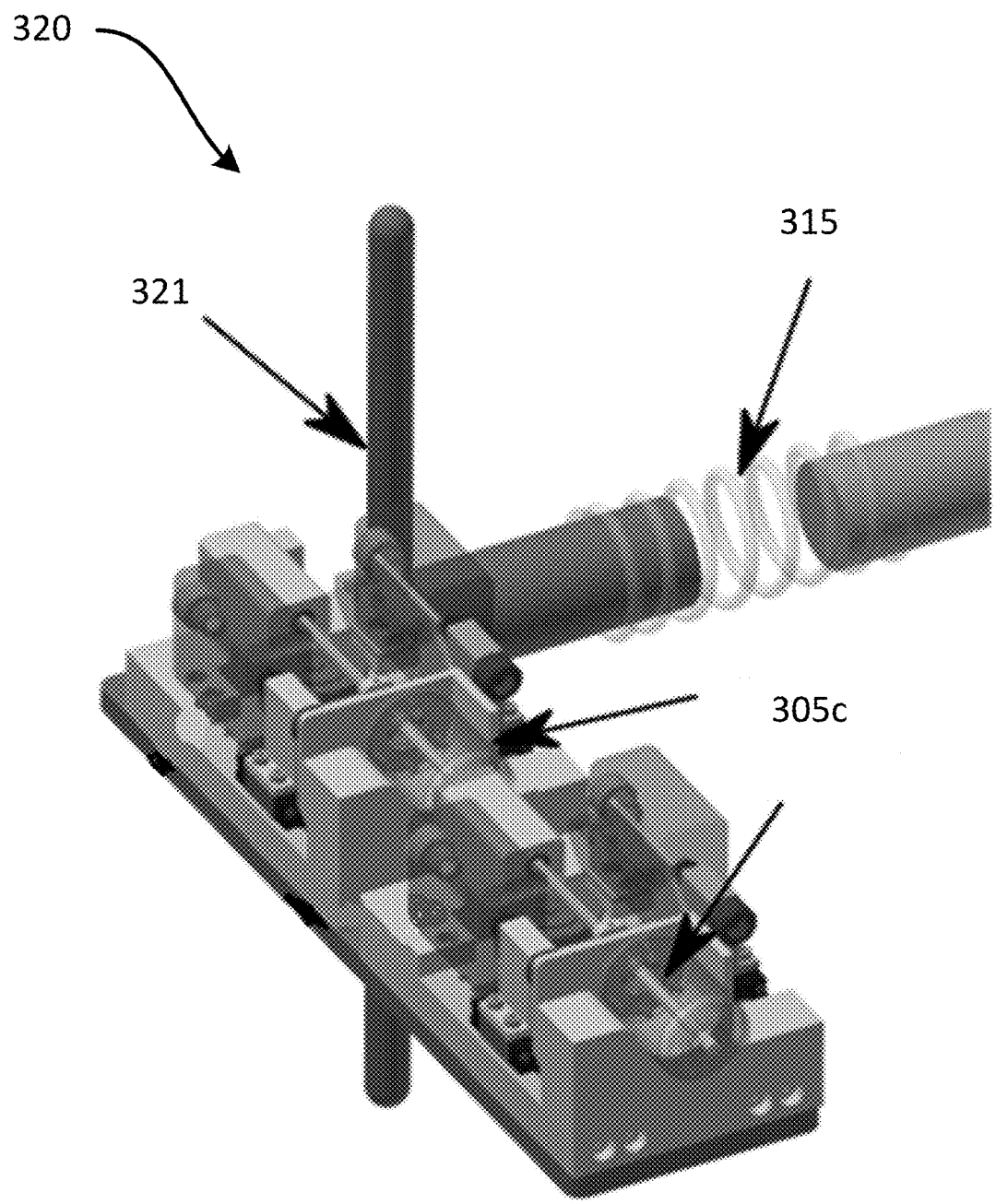

FIG. 3b shows a guidewire actuation assembly 320 for controlling the distal degrees of freedom of the guidewire tip, in accordance with one or more embodiments of the present invention. The guidewire actuation assembly 320 can be attached to a shaft 321 and elastic coupling 315 to facilitate the motion of the entire guidewire actuation assembly 320 inside the spiral groove 325 (shown in FIG. 3a). In some embodiments, the elastic coupling 315 can have significant torsional as well as bending rigidity to prevent deformation in the roll, pitch, or yaw directions. For instance, in some embodiments the elastic coupling 315 can be an elastic coil (e.g. a high-stiffness spring) composed of, for example and not limited to, plastic, brass, nitinol, titanium, or stainless steel. Additionally, the elastic coupling 315 can facilitate extension of the elastic coil as the guidewire actuation assembly 320 traverses the spiral groove and the guidewire is drawn out of the spiral groove. In other words, the elastic coupling 315 can extend as the guidewire actuation assembly 320 moves further away from the center of the spiral groove 325. The shaft 321 and elastic coupling 315 can allow for the entire guidewire actuation assembly 320 to be guided in the spiral groove 325 with low friction and sufficient clearance. In some embodiments, a bearing assembly can be attached on the top and bottom of the guidewire track. The bearing assembly can be in contact with the inner track of the spiral groove 325 (due to the elastic coupling being in tension) to facilitate smooth motion of the guidewire actuation assembly 320 along the spiral groove 325 and enable rigidity of the overall system and prevent it from wedging. In some embodiments, the bearing assembly can comprise a sealed radial bearing assembly. Storing the entire length of the guidewire in a concealed spiral track 317 can keep the overall system compact and prevent the need for a long linear storage enclosure (and hence a lower mass) for the system. In some embodiments, the spiral track 317 and the spiral groove 325 can be 3-D printed.

Figure 3C:
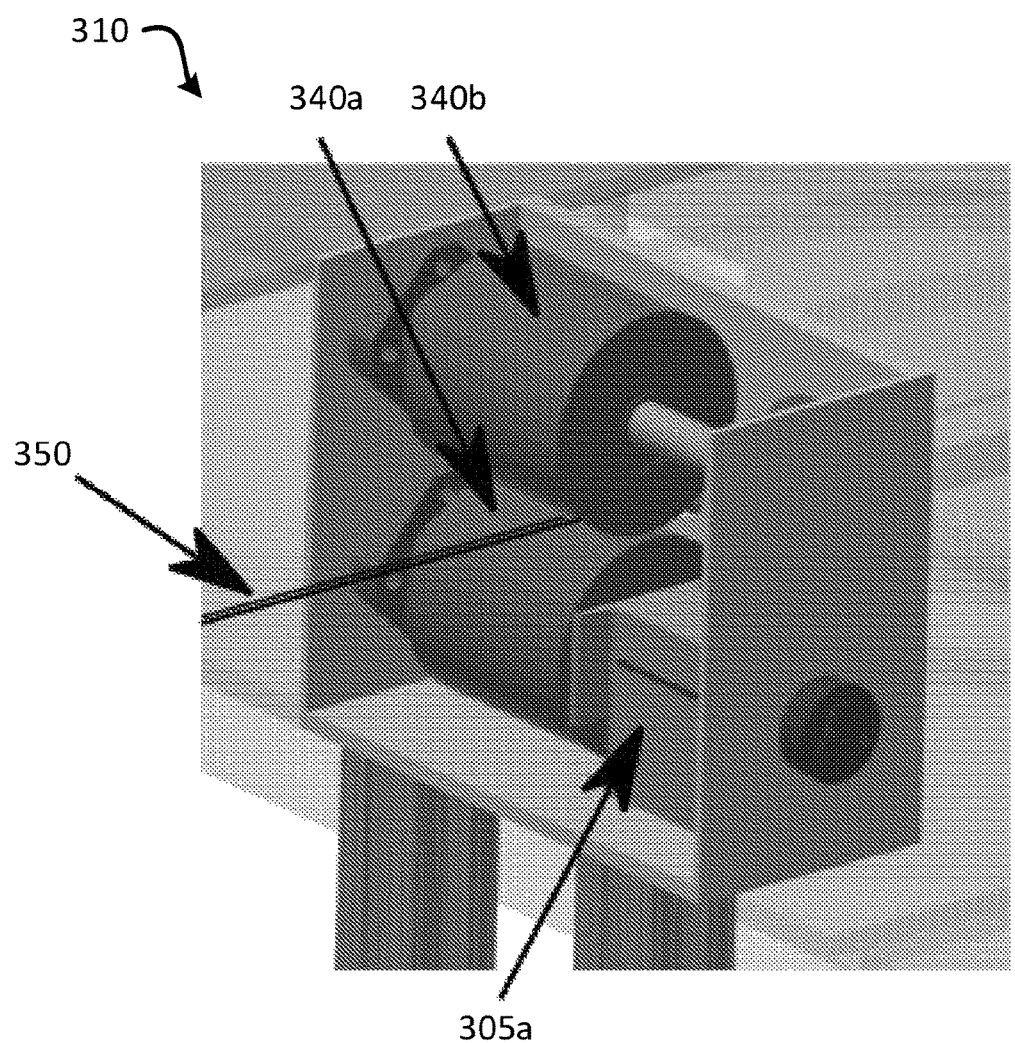

In some embodiments, advancement of the guidewire inside, for example, vasculature can be controlled by controlling the motion of motor 305b and the corresponding roller of the guidewire roller mechanism 310 attached to motor 305a. FIG. 3c shows an exemplary guidewire roller mechanism 310. In some embodiments, the guidewire roller mechanism 310 can include rollers 340a, 340b which can advance the guidewire by virtue of synchronized movement of motor 305a and motor 305b with proportional speed.

As seen in FIG. 3c, motor 305a can actuate one degree of freedom, namely for back and forth motion in a plane. When the motor 305c is commanded to move, it will move the linear stage, which in turn will move the opposing tendon in the opposite direction, thereby maintaining tension in the system. By coupling similar motion capability in close proximity, but in different planes, motion of the distal end of the tool can be achieved in three dimensions. This can, for instance, enable the physician to "steer" around a plaque or maneuver in a tight space.

To minimize or eliminate intra-joint as well as inter-joint coupling during motion of a specific degree of freedom of the distal end of the guidewire, it is critical to route the tendons appropriately within the guidewire. Routing of the guidewire tendons can be facilitated by making microgrooves in the body of the guidewire, to achieve decoupled joint motion. Since the diameter of the guidewire is negligible compared to the length of the joint and the radius of curvature, routing can ensure that the direction of the force exerted by the tendon on the joint allows flexion-extension of the joint and stiffness control. In some embodiments, this can be achieved by incorporating a wedge before the proximal end of the guidewire tip, that allows the proximal tendons to be routed before attaching to the proximal joint, thus allowing stiffness control for that specific degree of freedom. In some embodiments, wedges can be placed along the length of the guidewire to enable clear tendon separation and minimize inter-joint and intra-joint coupling.

While the above embodiments are discussed in terms of the guidewire tip, the use of guidewire tip may refer to the tip of a guidewire or a separable piece to be added onto the guidewire. As such, the above-described characteristics may be applicable to both the guidewire tip and the guidewire.

EXAMPLES

Example 1

Figure 4:
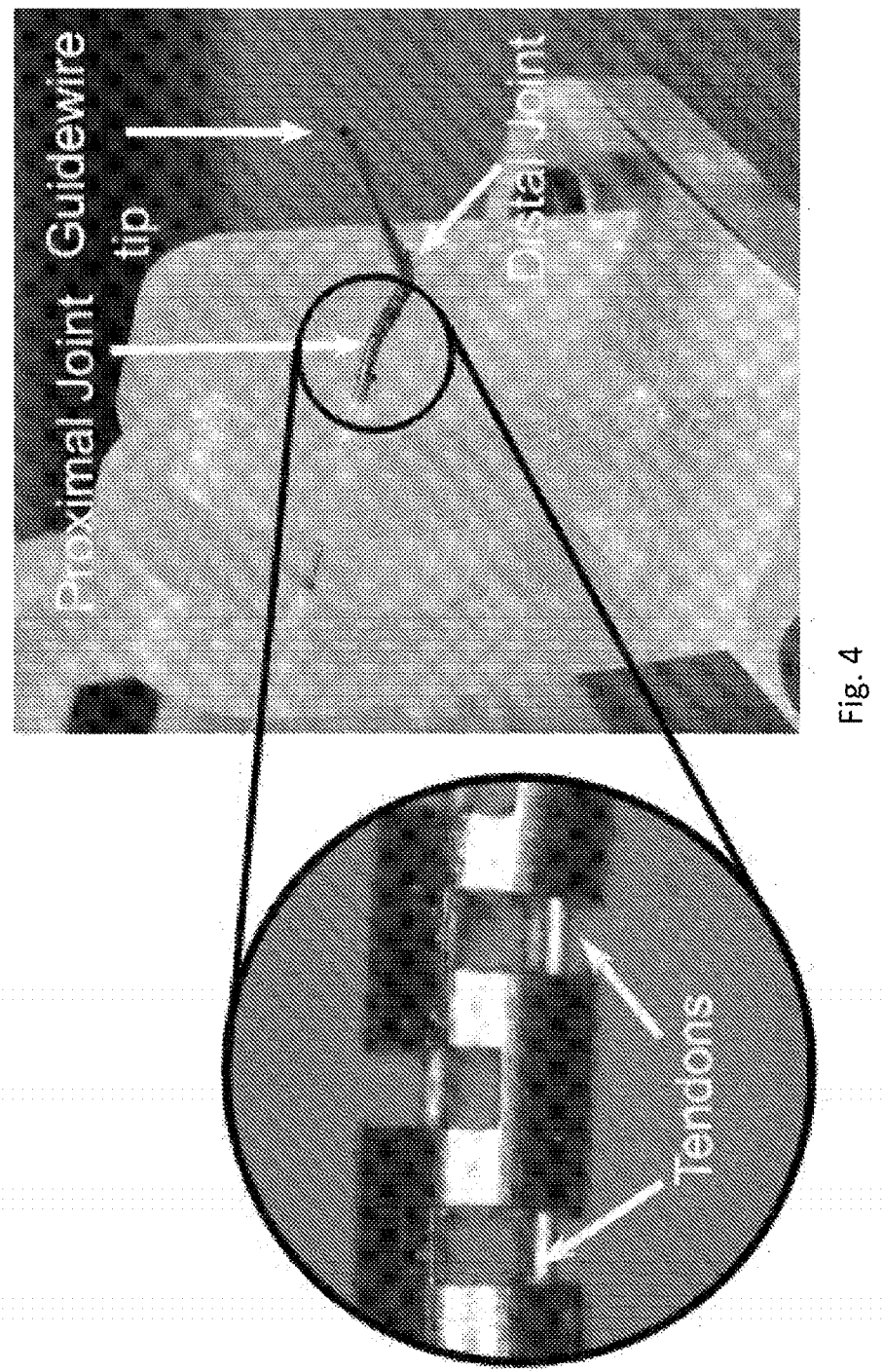
FIG. 4 shows a schematic of a two degree of freedom micro-scale guidewire tip using orthogonally oriented recesses, in accordance with an exemplary embodiment of the present disclosure.
Figure 5:
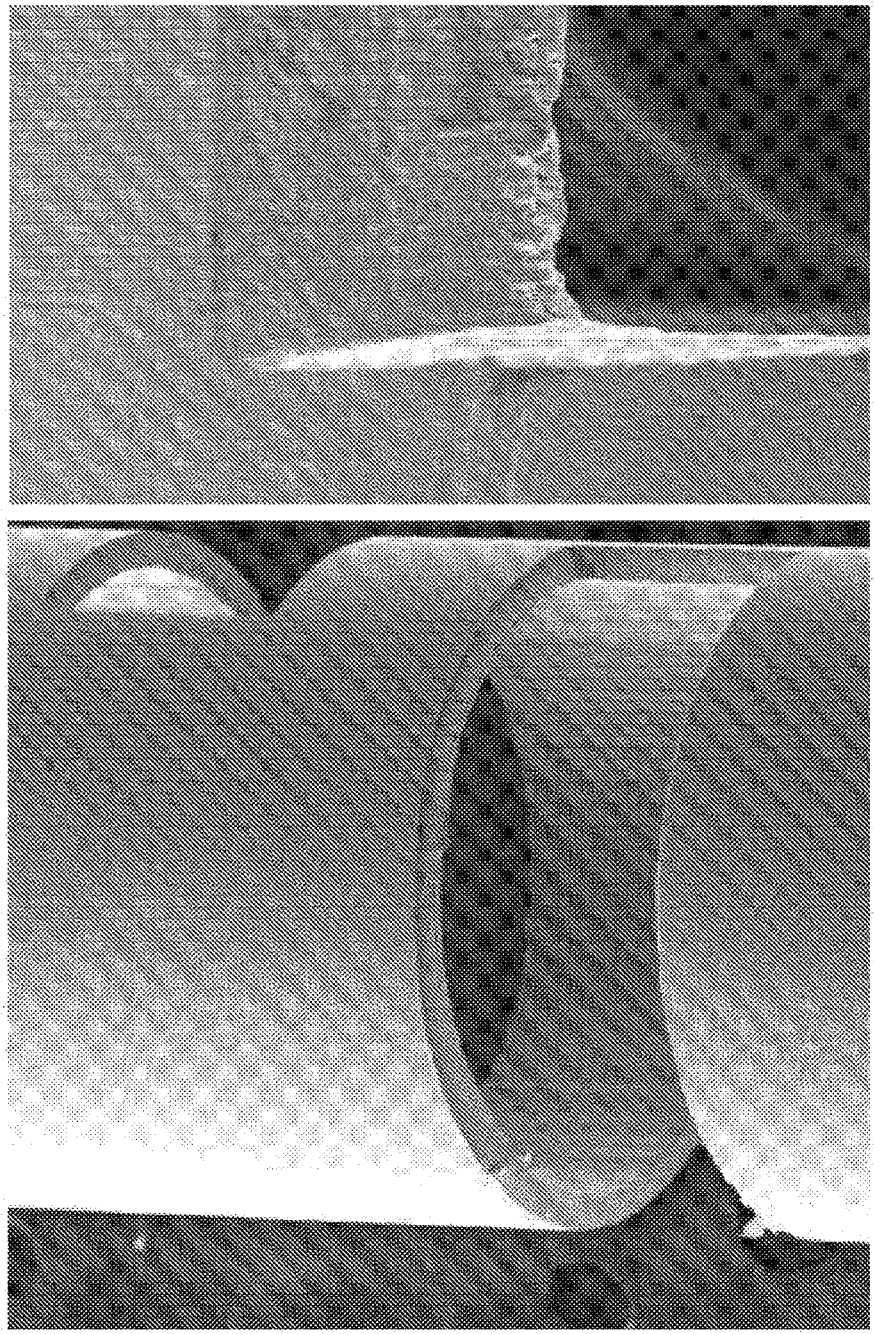
FIG. 5 shows Scanning Electron Microscope (SEM) images of a machined Nitinol tube showing minimal heat-affected zone, in accordance with an exemplary embodiment of the present disclosure.

In an exemplary embodiment, the guidewire tip can be robotically driven and contain two degrees-of-freedom. Each degree-of-freedom can be controlled by two tendons that permit the joint to be controlled bi-directionally. Each pair of tendons controlling a joint can be attached to the distal end of that joint. As a result, a total of four tendons can be routed through the inner lumen of the robot, as shown for example in FIG. 4. As can be seen in FIG. 4, the guidewire tip can be constructed from a single tube of Nitinol by etching recesses into the tube. To manufacture the guidewire tips, an Infrared Femtosecond Laser (Resonetics Corporation, Massachusetts, United States) was used to cut rectangular the recesses into a Nitinol tube of an outer diameter of 0.78 mm and inner diameter of about 0.62 mm (Confluent Medical, California, United States). The raw Nitinol tube was placed in a lathe chuck to permit the rotation of the tube between the etching of joints, thus allowing the finished robot body to be constructed without physically extracting the part from the laser, thus minimizing positioning errors. This setup and the results under a scanning electron microscope are shown in FIG. 5. As can be seen in FIG. 5, the usage of femtosecond laser pulses can minimize the heat-affected zone (HAZ) around the recesses, therefore allowing the micromachining process to occur without accidental treatment of the material.

The creation of recesses in the Nitinol tube can permit the tube to be bent in the plane of the recesses, thus creating a joint at the location of the recesses. By rotating the tube between joints, the orientation of these joints can be modified. Here, the raw tube was rotated by $$\frac{\pi}{2}$$

between joints, thus orienting the joints orthogonal to each other (see, e.g. FIG. 1*c*). Finally, Nitinol tendons with 0.1 mm diameter (Confluent Medical, California, United States) can be manually routed into the tube and the ends bonded to the outer walls of the Nitinol tube. Relevant assumptions for this model include 1) positive tension is applied to these tendons when they are pulled, and the tendons are incapable of exerting a negative tension on the tube; and 2) that the tendons exert a point force at their attachment point at the inner wall of the tube, and a constant reaction force along the wall of the tube.

To minimize coupling between the joints, tendon-driven continuum robots often use a variety of load decoupling strategies. For instance, embodiments of the present disclosure can achieve 'controlled load-coupling' of the tendons through the inner lumen. This is achieved by inserting a rigid Nitinol strip (termed the routing wedge as illustrated in FIG. 1*c*). As seen in FIG. 4, one tendon of the proximal joint and one tendon of the distal joint can be routed through each of the two openings of the routing strip. As a result, a repeatable inter-joint load-coupling in the robot can be achieved, while keeping the manufacturing cost of the robot low. More complex routing mechanisms would be able to achieve a lower level of load-coupling between the proximal and distal joints, but would result in a longer manufacturing time.

Joint and Robot Model

Each joint of the underactuated robot can be modeled as having a piecewise-constant curvature, which enables ease of robot-independent kinematic transformations.

Figure 6A:
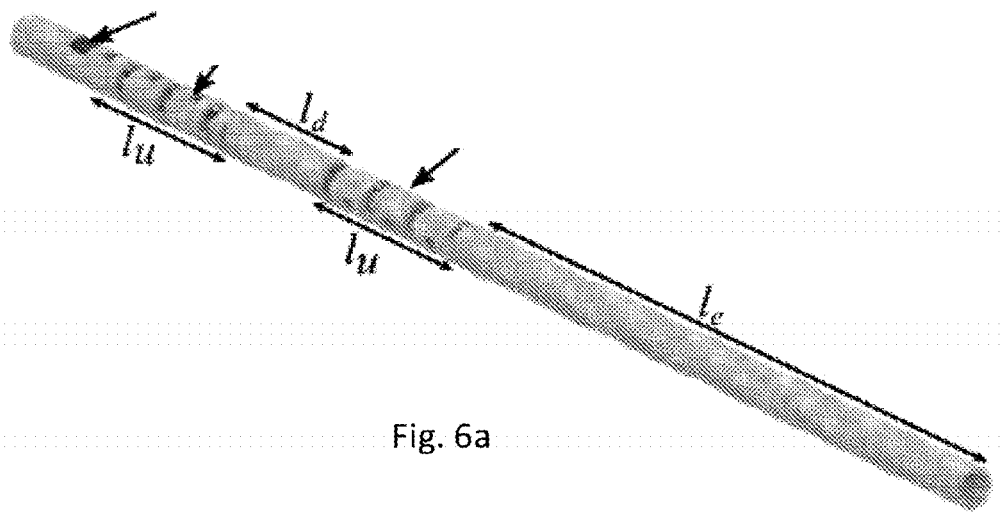
FIGS. 6*a* and 6*b* show forward kinematic models of a joint both in an undeformed state and a deformed state, in accordance with an exemplary embodiment of the present disclosure.
Figure 6B:
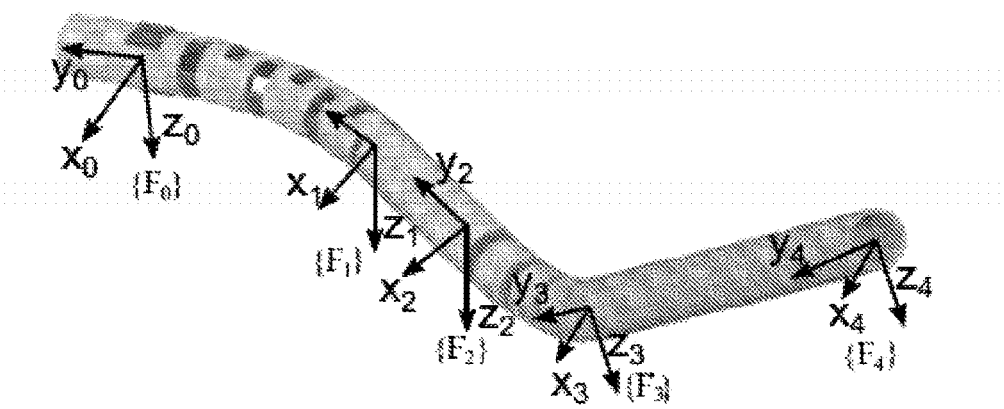

The dimensions associated with the kinematics of an exemplary guidewire tip are defined in FIG. 6*a*, and the associated frames are denoted in FIG. 6*b*. The initial (undeformed) length of each joint can be denoted by $l_u$. When the proximal joint is actuated by the tendon, it deforms by an angle θ. The curvature of this joint can be defined as $$\kappa_1 = \frac{\theta}{l_u},$$

and the homogeneous transformation matrix for this joint is given as, $$B_1^0 = \begin{bmatrix} C_\theta & -S_\theta & 0 & \frac{1-\cos\theta}{\kappa_1} \\ S_\theta & C_\theta & 0 & -\frac{\sin\theta}{\kappa_1} \\ 0 & 0 & 1 & 0 \\ 0 & 0 & 0 & 1 \end{bmatrix}$$

where C and S denote the cosine and sine functions, respectively. Unlike most continuum manipulators that have co-located degrees of freedom, the second degree-of-freedom of the manipulator is located is a certain distance $l_d$ from {F1}. This degree-of-freedom allows the robot to move out of the $x_0$-$\mathcal{Y}_0$ plane by an angle φ and its curvature is defined as $$\kappa_2 = \frac{\varphi}{l_u}.$$

Therefore, the final transformation to the base of the robot from the tip can be formulated as follows:

$$B_4^0 = B_1^0 \cdot B_2^1 \cdot B_3^2 \cdot B_4^3 \qquad (2)$$

-continued $$B_2^1 = \begin{bmatrix} 1 & 0 & 0 & 0 \\ 0 & 1 & 0 & -l_d \\ 0 & 0 & 1 & 0 \\ 0 & 0 & 0 & 1 \end{bmatrix} \qquad (3)$$

and $B_3^2$ arrives at $\{F_2\}$ from $\{F_3\}$, $$B_3^2 = \begin{bmatrix} 1 & 0 & 0 & 0 \\ 0 & C_\varphi & -S_\varphi & -\frac{\sin\varphi}{\kappa_2} \\ 0 & S_\varphi & C_\varphi & \frac{\cos\varphi - 1}{\kappa_2} \\ 0 & 0 & 0 & 1 \end{bmatrix} \qquad (4)$$

Figure 7:
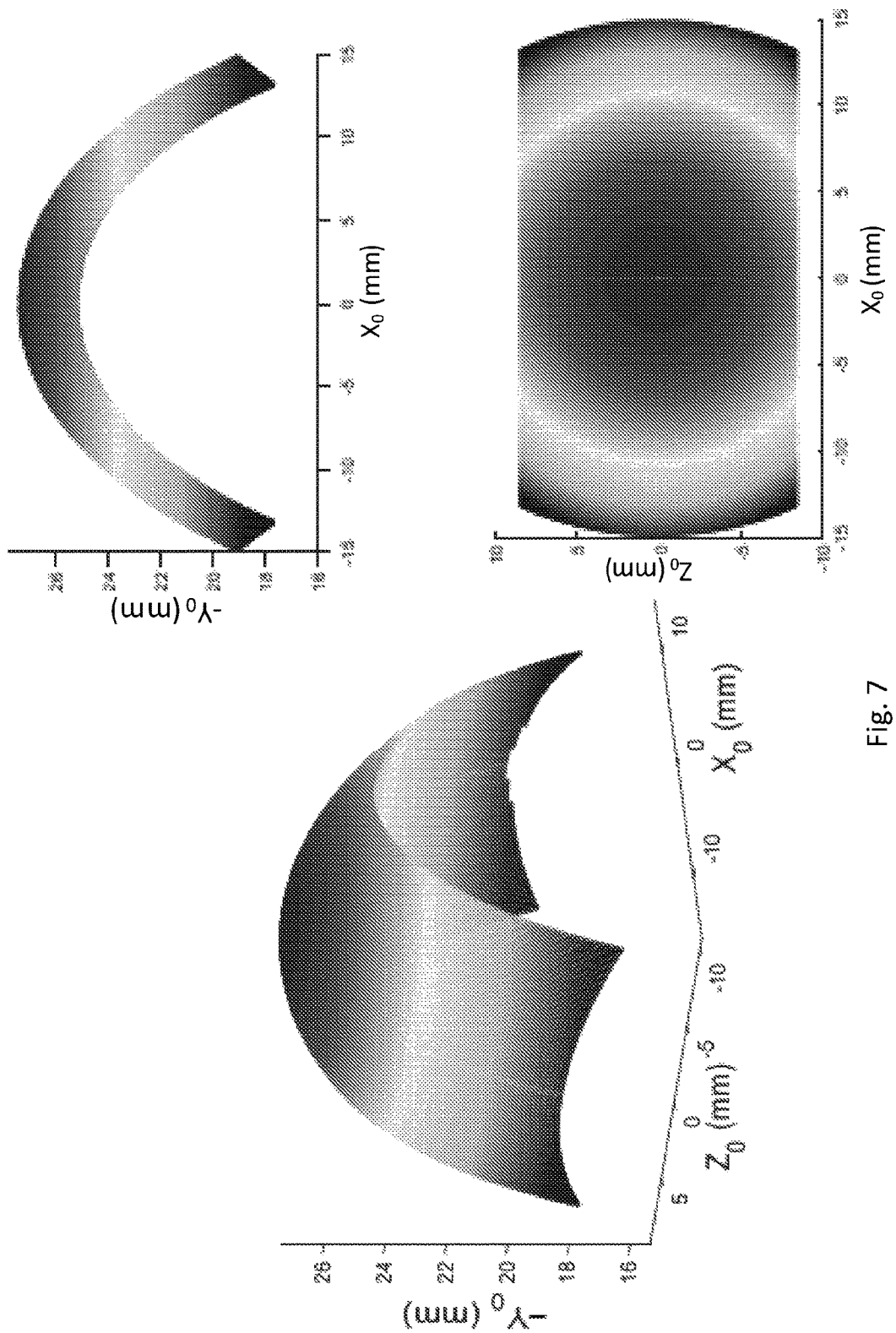
FIG. 7 shows the workspace of a robotic guidewire, in accordance with an exemplary embodiment of the present disclosure.

Finally, $B_4^3$ involves a simple translation from $\{F_4\}$ to $\{F_3\}$, along $-\mathcal{Y}_3$ by length $l_e$. Ignoring the orientation at the tip of the guidewire, and assuming a given task-space reference input $[p^o, 1]^T \in \mathbb{R}^4$, $$\begin{bmatrix} p^0 \\ 1 \end{bmatrix} = B_4^0 \begin{bmatrix} 0^4 \\ 1 \end{bmatrix} \qquad (5)$$

where $o^4 \in \mathbb{R}^3$ is the origin in the $\{F_4\}$. Using the dimensions of the guidewire tip prototype, the workspace of the robot tip is generated and displayed in FIG. 7.

For the controller to follow predefined trajectories, the inverse kinematics of the guidewire must first be defined. Eq. 5 results in the following equations, $$\mathcal{P}_x^0 = l_e \sin\theta \cos\varphi + \frac{\sin\theta \sin\varphi}{\kappa_2} + l_d \sin\theta + \left(\frac{1-\cos\theta}{\kappa_2}\right) \qquad (6)$$

and subsequently,

The two unknowns $\theta$ and $\varphi$, and therefore, the curvatures ($\kappa_1$, 78 $_2$) can be derived numerically using the above equations. It can be assumed that the initial values of the joint angles are $$\theta_{initial} = \arctan\left(\frac{p_x^o}{2l_u + l_d + l_e}\right) \text{ and } \varphi_{initial} = \arctan\left(\frac{p_z^o}{l_u + l_e}\right),$$

so that $\theta_{initial} \leq \theta$ and $\varphi_{initial} \leq \varphi$, and increment joint angles until the correct values are obtained.

Joint Kinematics and Statics

In addition to the geometric kinematics discussed above, a sufficient understanding of each joint comprising the robot must be developed. This includes a mapping from the joint curvature to the tension applied at the base of the joint. Traditionally, a mapping from the configuration space ($\kappa$) to the actuator space parameters (u) is considered. However, there is a large variance introduced in this relationship by extremely small changes in the tendon path through the lumen of the tube especially at the point where it is bonded to the wall of the Nitinol tube. On the other hand, the tension-curvature relationship is more repeatable and consistent. Here, it is assumed that a single tendon is routed straight to distal end of the base joint of the robot.

Moment-Curvature Relationship

The bending angle of the joint results from the deformation of each recess that is formed by two tubes and a curved wall, as shown in FIG. 8*a*. The figure shows that the curved wall has little bending deformation and the tubes have obvious transverse deformation that is orthogonal to the bending plane (FIG. 8*b*). The contraction and expansion of the tube change the dimension of each layer of the tube, which generates a bending angle for the tube in the transverse direction. By observation, the bending angle of each recess mainly comes from bending angles of tubes. Simplified linear static models of the curved wall and tubes can be used to show the concept.

The joint curvature $\kappa$ that is proportional to the total bending angle of the recess joint can be approximated by superposition of bending angles of all tubes in the recess, which indicates a linear relationship between the curvature $\kappa$ and tendon force P, $$\kappa = d \cdot E_b \cdot P \qquad (7)$$

where $E_b$ can be defined as the bending elasticity of the joint. Although an analytical model can provide a theoretical explanation about the bending behavior of the recess joint, an accurate value of $E_b$ can be estimated from experiments presented later.

Friction Effects

The above moment-curvature relations were developed with a setup that was designed assuming negligible friction effects. However, in a realistic situation, where two tendons are attached to the recess joint, and are not directly routed to the attachment point, the effects of friction in this relationship could be observed. Due to the small diameter of the robot and the tendons controlling the robot, tendon tension can be measured only at the attachment point of the tendons to the actuators. As a result, friction must be incorporated into the moment-curvature relationship defined above. A Coulomb friction model was used to estimate the relationship between the measured tendon tension ($\tau$) and the tension applied at base of the joint (T), $$\tau = T \cdot e^{\mu \cdot \alpha \cdot sgn(v)} \qquad (8)$$

where $\mu$ is the coefficient of friction of the routing channel, $\alpha$ is the wrapping angle and $v$ is the tendon velocity. Therefore, the relationship between the sensed tension and the joint curvature is given by, $$\kappa = E_b \cdot \frac{d \cdot \mathcal{T}}{e^{\mu \cdot \alpha \cdot sgn(v)}}. \qquad (9)$$

The hysteresis in FIG. 8 for differing values of wrapping angle displays a linear $\tau$-$\kappa$ relationship for both positive and negative values of $v$. The slopes of these linear curves can therefore be expressed as $$\Gamma_b(v, \alpha) = \frac{d \cdot E_b}{e^{\mu \cdot \alpha \cdot sgn(v)}}.$$

Figure 9:
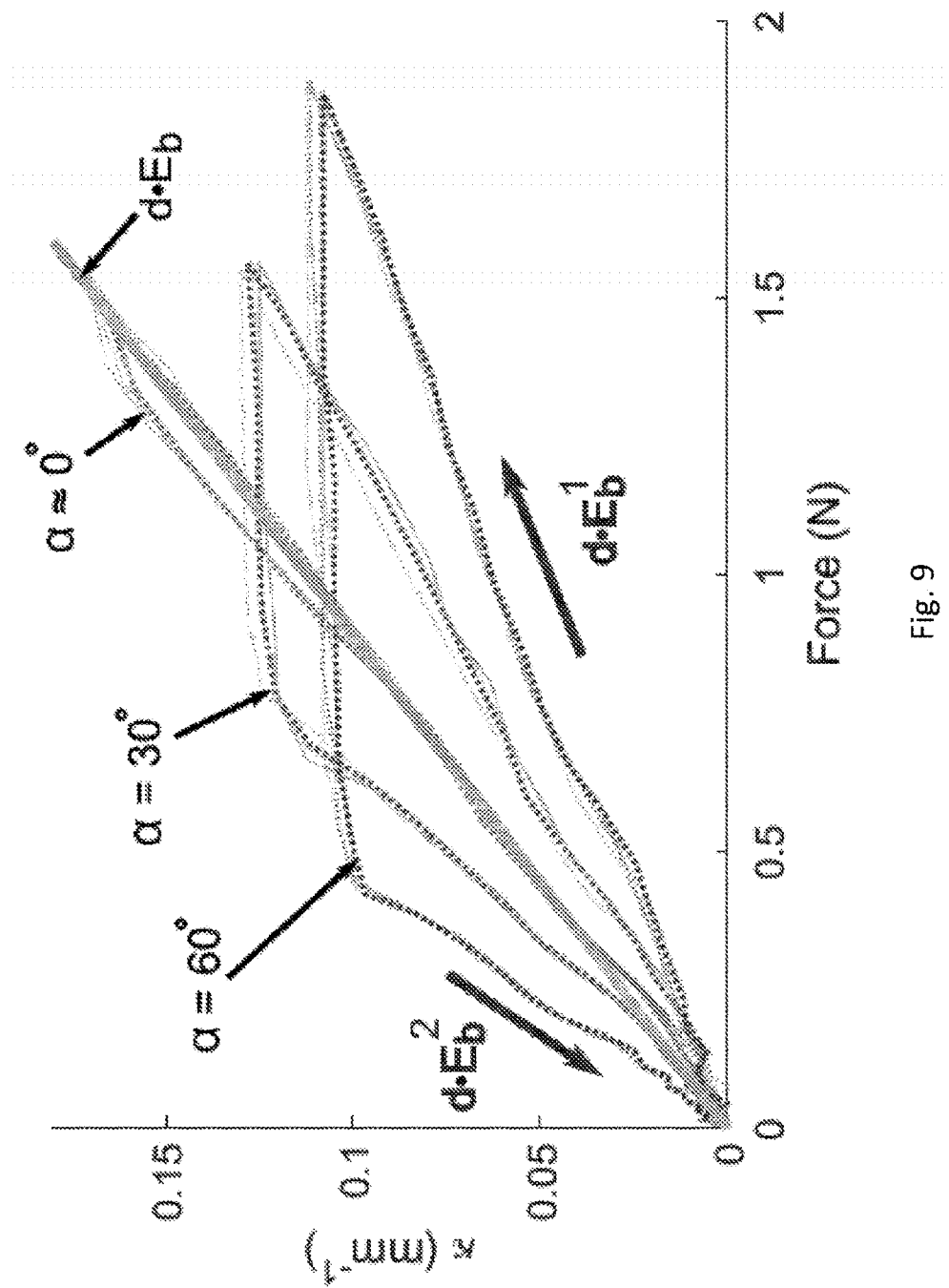
FIG. 9 shows a graphical representation of the hysteresis seen in the tendon tension ($\tau$) versus joint curvature ($\kappa$) relationships for various values of wrapping angle ($\alpha$) which help in estimating coefficient of friction ($\mu$) and the bending elasticity ($E_b$) of the base joint, in accordance with an exemplary embodiment of the present disclosure.

For the hysteresis loop of angle $\alpha$, two slopes $E_b^1$, and $E_b^2$ can be defined, as displayed in FIG. 9. Assuming $$E_b^1 = \frac{d \cdot E_b}{e^{\mu \cdot \alpha}} \text{ and } E_b^2 = \frac{d \cdot E_b}{e^{-\mu \cdot \alpha}}.$$

Since the slopes $E_b^1$, $E_b^2$ are known, the value of $E_b$ is extracted as $$E_b = \frac{\sqrt{E_b^1 E_b^2}}{d} \quad (10)$$

As seen in FIG. 9, that for various wrapping angles, this value of joint bending elasticity ($E_b$) stays constant. As specified previously, each joint of the robot has two tendons attached to its distal end for bidirectional control. As a result, two wrapping angle values ($\alpha_1$, $\alpha_2$) associated with the base joint of the robot are used.

Coupling Effects

Figure 10:
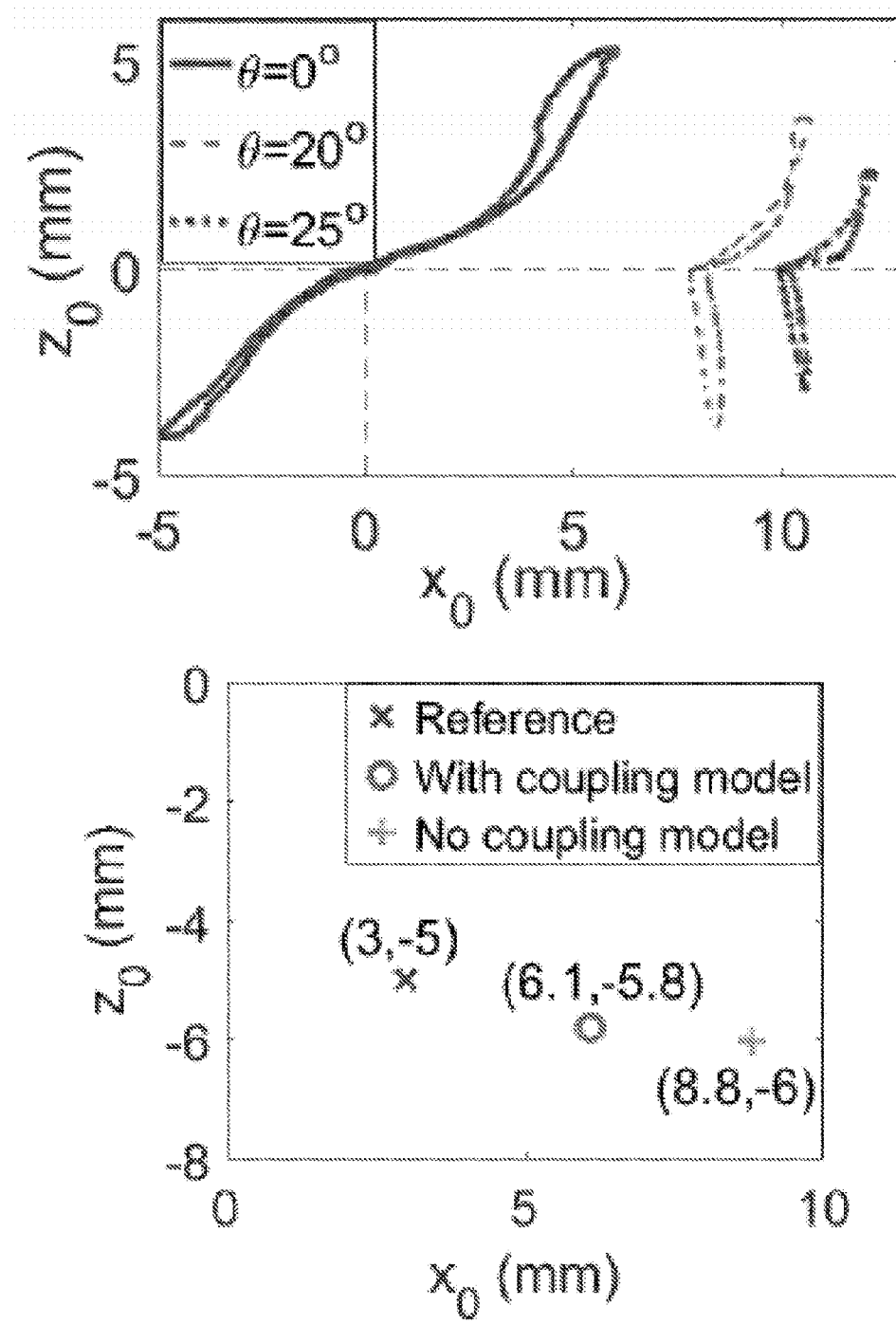
FIG. 10 shows graphical representations of the projection of the guidewire tip on $x_0$-$z_0$ plane indicates coupling seen between the two degrees of freedom of the guidewire (top) and use of a coupling model minimizes the steady state error in two degrees of freedom (bottom), in accordance with an exemplary embodiment of the present disclosure.

Due to the tendon routing described previously, distal tendons impart a moment on the proximal joint, causing an inter-joint load-coupling to exist by design. In the absence of such coupling, actuating the distal joint without any actuation of the proximal joint should only cause the tip of the robot to move in the $y_0$-$z_0$ plane. As a result, a projection of the robot tip on the $x_0$-$z_0$ plane should result only in motion along the $z_0$ axis. However, a projection of the robot tip on the $x_0$-$z_0$ plane was observed to result in motion along both the axes (see FIG. 10 (top), solid line). This phenomenon was also noted when the proximal joint was pre-bent to a non-zero value of joint angle ($\theta \neq 0$) (see FIG. 10 (top), dashed lines). This shows that pure actuation of the distal joint also causes additional bending in the proximal joint. To model the inter-joint coupling, Eq. 15 can be modified as follows:

$$\underbrace{\begin{bmatrix} \kappa_1 \\ \kappa_2 \end{bmatrix}}_{k} = d \cdot \underbrace{\begin{bmatrix} 1 & 1 \\ 0 & 1 \end{bmatrix}}_{C} \cdot \underbrace{\begin{bmatrix} E_b & 0 \\ 0 & E_b \end{bmatrix}}_{E_{bending}} \cdot \underbrace{\begin{bmatrix} T_1 \\ T_2 \end{bmatrix}}_{T} \quad (11)$$

where $T_i$ is the tension applied at the base of the joint i. This relationship can be used to place the tip in the 2-degree of freedom space. A coupling model improves the steady-state error in 2 degrees of freedom, where the Euclidean norm of the error decreases from 6.1 mm to 3.2 mm.

Control System

Figure 11:
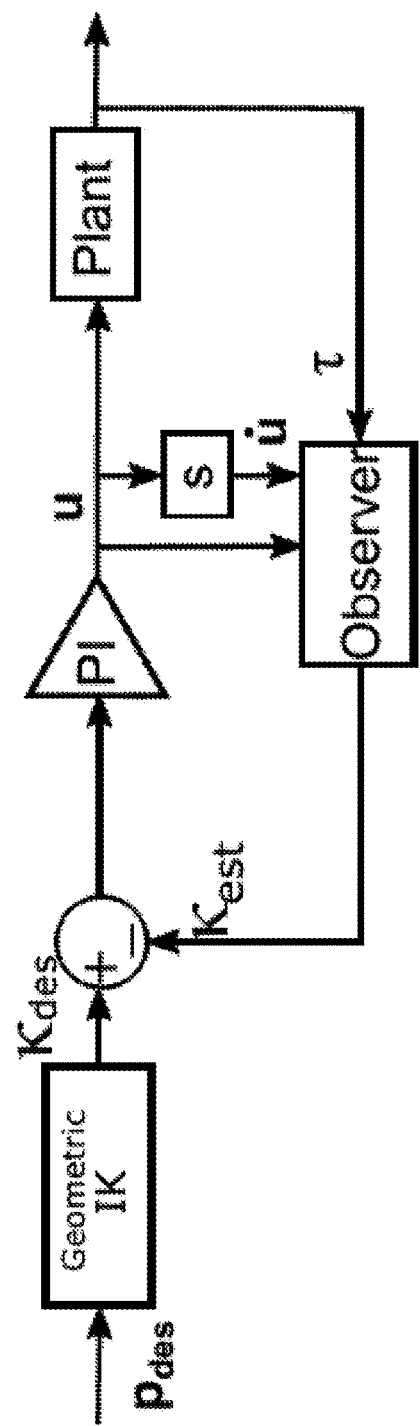
FIG. 11 shows a closed loop control system to perform position control on the guidewire base-joint-space variables, in accordance with an exemplary embodiment of the present disclosure.

A controller can be used to take advantage of the moment-curvature relationship defined previously to control the base joint of the robot. The task space can be defined as the $x_0$-$z_0$ plane (while the operational space of the robot is still $\mathbb{R}^6$). The proposed controller for this task space trajectory control of the robot tip is shown in FIG. 11. Consecutive points along a trajectory in the $x_0$-$z_0$ plane are provided as input ($P_{des}$) to the Geometric Inverse Kinematics algorithm defined above. This computation results in a desired curvature $\kappa_{des}$, that is then compared with the output of an observer that outputs the most recent state estimate $\kappa_{est}$. A PI controller for the actuator displacement is designed as $u = K_p^e + K_i \int e \, dt$, where $e = (\kappa_{des} - \kappa_{est})$.

Observer Design

The Observer Block in FIG. 11 is designed to use the moment-curvature relationships to estimate the shape of the robot. Using the friction model defined above, a piecewise linear observer was designed that uses the following relationships to estimate the base joint curvature $\kappa_{est}[n]$ at the $n^{th}$ discrete time step, $$\kappa_{est}[n] = \begin{cases} d \cdot \Gamma_{piecewise}(u, \dot{u}, n) \cdot \tau[n], & \text{if } \text{sgn}(u[n]) = \text{sgn}(\dot{u}[n-1]) \\ \kappa_{est}[n-1], & \text{else if } \tau[n] \in [\tau_{min}, \tau_{max}] \\ d \cdot \Gamma_{piecewise}(u, \dot{u}, n) \cdot \tau[n], & \text{else} \end{cases}$$

Figure 12:
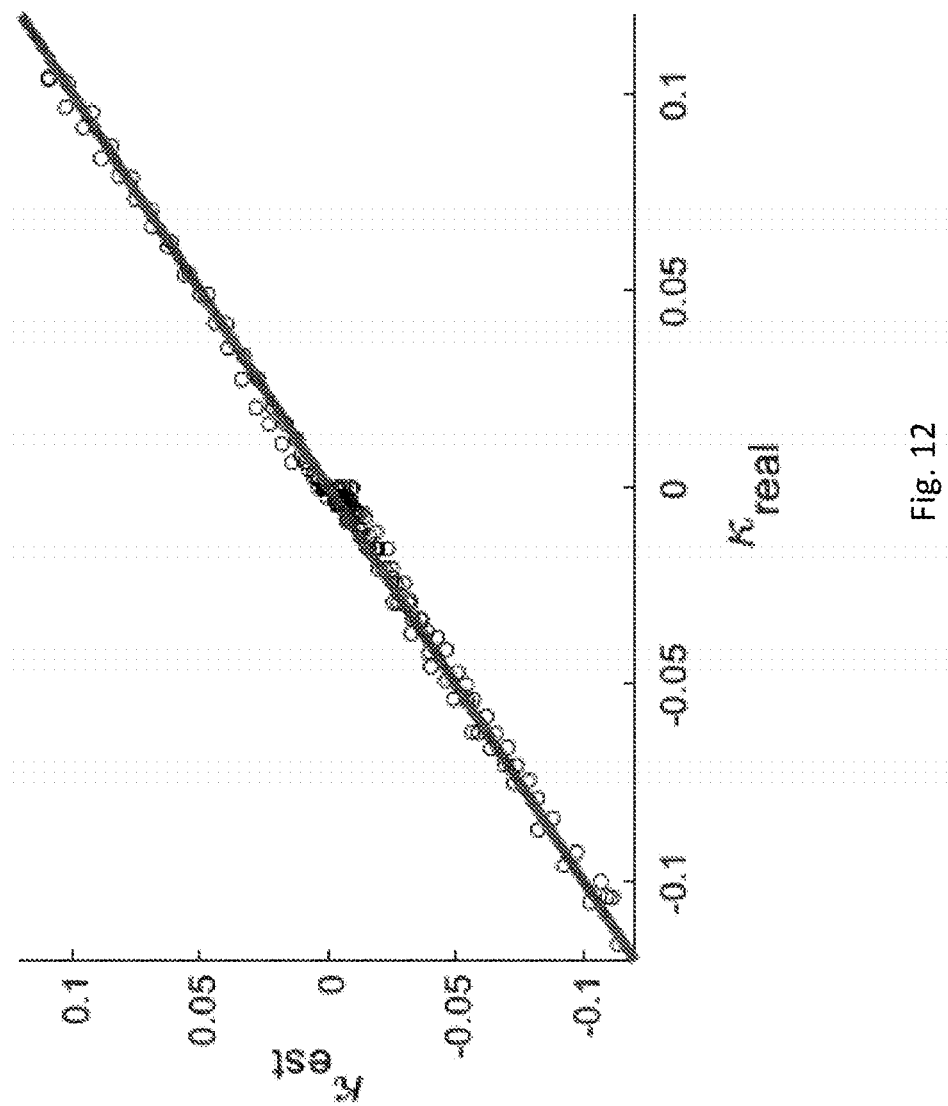
FIG. 12 shows a graphical representation of the ground truth curvature ($\kappa_{real}$) vs. the estimate curvature by the observer developed ($K_{est}$), sampled during a set of random trajectories provided to the system, in accordance with an exemplary embodiment of the present disclosure.

Here, $[\tau_{min}, \tau_{max}]$ which is the range of forces, for which the hysteresis curve plateaus are computed at each point in time. Also, the bending elasticity function $\Gamma_{piecewise}(u, \dot{u}, n)$ is different from the term $\Gamma b$ defined previously, and can be defined as follows:

$$\Gamma_{piecewise}(u, \dot{u}, n) = \begin{cases} \Gamma_b(\alpha_1, \dot{u}), & \text{if } \text{sgn}(u[n]) > 0 \\ \Gamma_b(\alpha_1, \dot{u}), & \text{else} \end{cases}$$

Where $\alpha_i$ is the wrapping angle of the tendon that is currently engaged. The observer was tested by providing a set of random trajectories to the system while sampling the curvature under a microscope at several points (see FIG. 12). Using this observer, a satisfactory estimate of the base joint curvature in either direction is obtained, and may be used as feedback in the control system.

Tracking Performance

Figure 13:
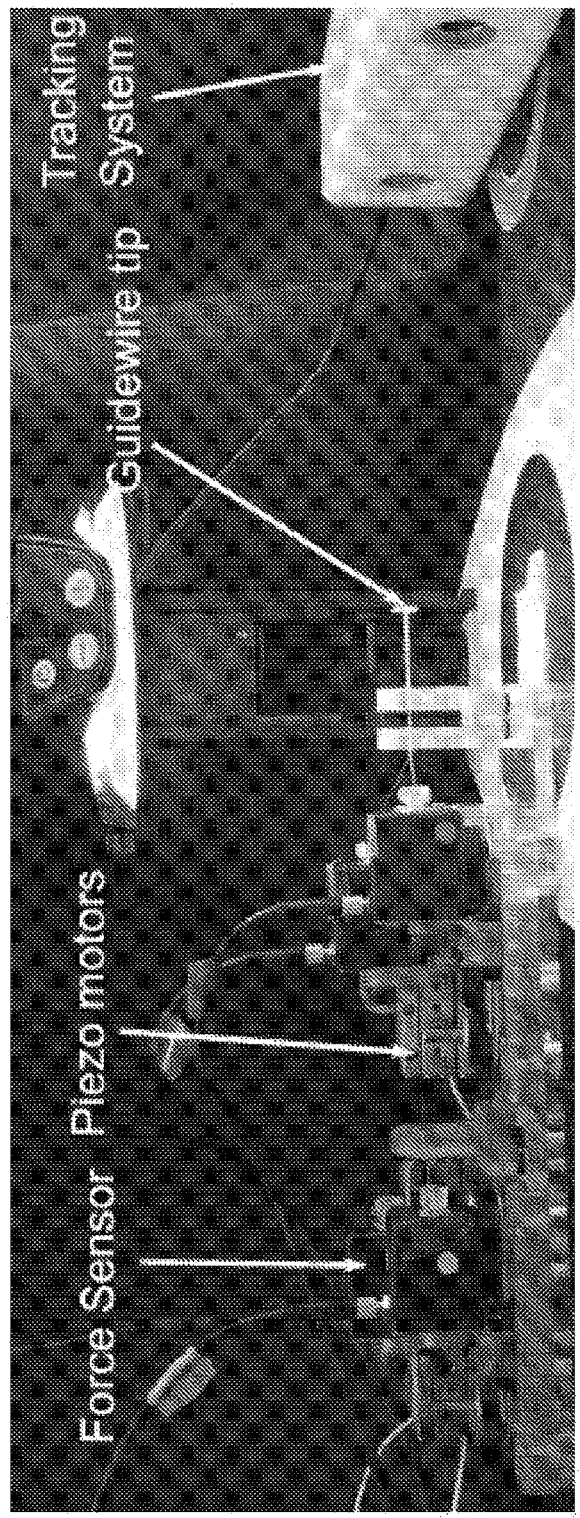
FIG. 13 illustrates an antagonistic motion-based controller hardware to test tracking accuracy of the system, in accordance with an exemplary embodiment of the present disclosure.

To test the controller, a compact setup was constructed as illustrated in FIG. 13. Each joint of the robot has two tendons bonded to its distal end, which on the actuator side terminate at an antagonistic transmission, which uses a single piezo-based linear actuator (SmarAct GmbH, Oldenburg, Germany). The transmission consists of a timing-belt and pulley arrangement that enables antagonistic motion of the two tendons in effect, similar to the ones used in previous robotic catheter controllers. Each tendon is bonded to the transmission via a load cell with a maximum load capacity of 5 pounds (Transducer Techniques, California, United States). The data from the force sensor, an encoder and the microscope are acquired via a 16-bit ADC (Model 826, Sensoray, Portland, United States) and UART respectively. An image processing algorithm that uses Hough transforms automatically provides the ground truth for the base joint curvature at each point of time. Lastly, a marker is attached to a tip, and a stereoscopic camera (MicronTracker H40, Toronto, Ontario, Canada) tracks the end of the guidewire prototype in the $x_0$-$z_0$ plane.

Figure 14A:
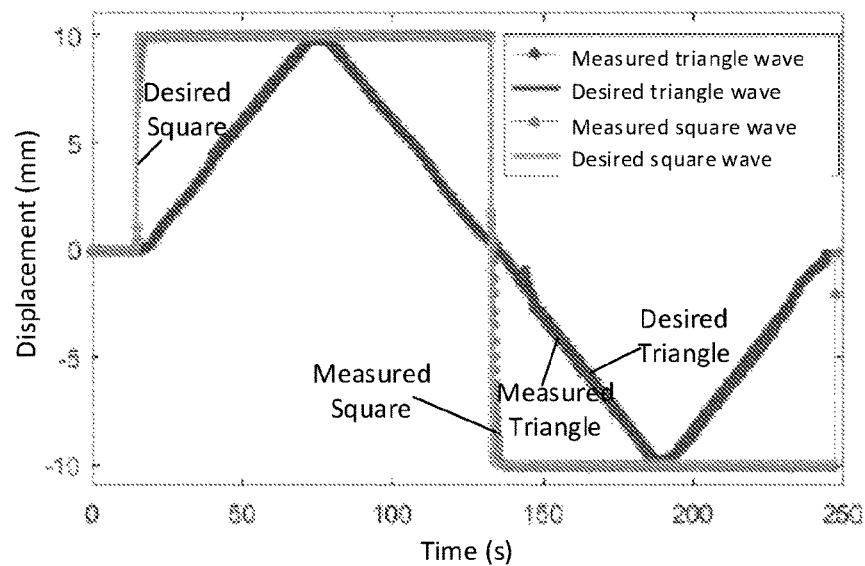
FIGS. 14*a* and 14*b* show graphical representations of the tracking results of the base joint for triangular and square reference inputs on the $x_0$ axis (top) and tracking results for sinusoids of varying frequencies (bottom), in accordance with an exemplary embodiment of the present disclosure.
Figure 14B:
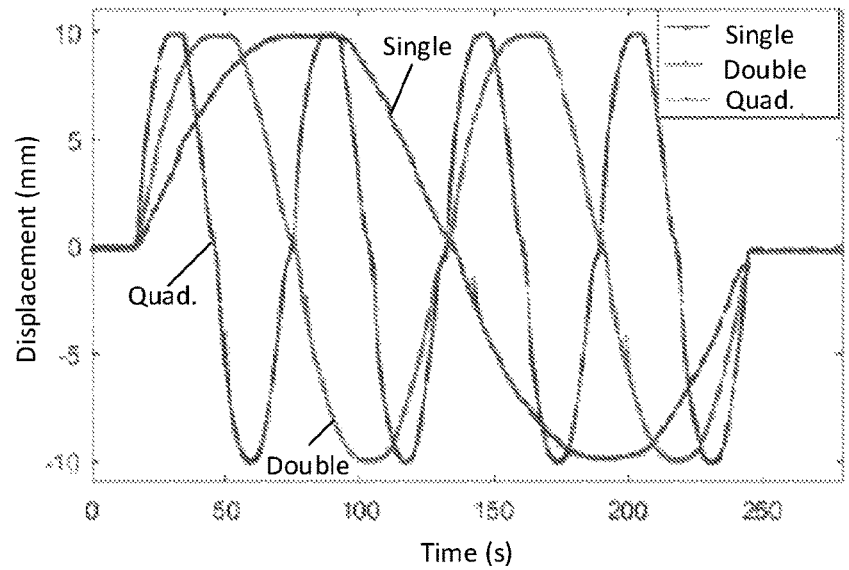

Next, three types of input profiles (sinusoidal, triangular and square trajectories) were provided in task space to the base joint controller. The time period of each input type was varied from 50 secs-250 secs. FIG. 14a-14b illustrates that the PI controller defined previously is able to track the input profiles closely, with negligible steady state error for each step input. Furthermore, it is also able to track at speeds often seen in a surgical environment.

We claim:

1. A system for steering a guidewire comprising:
   a continuous length of an elongate hollow body comprising:
      a first joint portion defined by a first set of asymmetric recesses formed in the elongate hollow body;
      a recess-free portion defined by an enclosed length of the elongate hollow body;
      slots disposed within the recess-free portion of the elongate hollow body; and
      a second joint portion defined by a second set of asymmetric recesses formed in the elongate hollow body;

wherein the first set of asymmetric recesses is offset from the second set of asymmetric recesses by from 1 to 180 degrees;
a tendon system comprising tendons operably connected to the first joint portion and the second joint portion;
a routing wedge disposed within the elongate hollow body spatially separating the tendons from one another; and
a control unit operably connected to the tendon system;
wherein the control unit is configured to actuate the tendon system to cause the first joint portion to bend in a manner providing a first degree of freedom of movement;
wherein the control unit is further configured to actuate the tendon system to cause the second joint portion to bend in a manner providing a second degree of freedom of movement different from the first degree of freedom of movement;
wherein the routing wedge comprises wedge portions receivable through the slots; and
wherein the received wedge portions define a central channel and outer channels.

2. The system of claim 1, wherein:
the tendon system comprises:
 a first tendon disposed within the elongate hollow body and operably connected to the first joint portion;
 a second tendon disposed within the elongate hollow body and operably connected to the first joint portion;
 a third tendon disposed within the elongate hollow body and operably connected to the second joint portion; and
 a fourth tendon disposed within the elongate hollow body and operably connected to the second joint portion;
a depth of the first set of asymmetric recesses and the second set of asymmetric recesses is greater than 50% of a width of the elongate hollow body;
the system is a robotically actuated system;
the control unit is configured to actuate the first tendon and the second tendon to cause the first joint portion to bend in the manner providing the first degree of freedom of movement; and
the control unit is further configured to actuate the third tendon and fourth tendon to cause the second joint portion to bend in the manner providing the second degree of freedom of movement.

3. The system of claim 1, wherein the elongate hollow body has a width from about 0.1 mm to about 0.9 mm; and
wherein the first set of asymmetric recesses is orthogonal to the second set of asymmetric recesses.

4. The system of claim 1, wherein the continuous length of the elongate hollow body comprises a continuous tubular body having an annular wall extending the length of the elongate hollow body; and
wherein the tendons are disposed within the tubular body, outside the annular wall.

5. The system of claim 1, wherein each of the tendons comprises a superelastic wire.

6. The system of claim 1, wherein each asymmetric recess of the first and second sets of asymmetric recesses has a shape selected from a group consisting of rectangular, triangular, and sinusoidal.

7. The system of claim 1, wherein the control unit comprises a guidewire actuation assembly and a guidewire roller mechanism;
wherein the guidewire actuation assembly comprises motors for advancing, retracting, and rotating the guidewire through the guidewire roller mechanism.

8. The system of claim 7, wherein the guidewire roller mechanism comprises a first roller and a second roller;
wherein the guidewire roller mechanism is operably coupled to a first motor;
wherein a portion of the guidewire is disposed between the first and second rollers;
wherein the control unit further comprises:
 a groove path for storing the guidewire; and
 a shaft operably coupled to an elastic coupling;
 wherein the shaft is operable by a second motor and configured to unspool the guidewire from the groove path to the guidewire roller mechanism.

9. A guidewire tip for steering a guidewire comprising:
a hollow elongated body including:
 a first joint comprising a first plurality of asymmetric recesses; and
 a second joint comprising a second plurality of asymmetric recesses;
 wherein the first joint and the second joint are co-located;
 wherein the first plurality of asymmetric recesses is offset from the second plurality of asymmetric recesses by from 40 to 130 degrees;
a first tendon, a second tendon, a third tendon, and a fourth tendon disposed within the hollow elongated body;
a routing wedge disposed within the hollow elongated body spatially separating the tendons from one another;
slots disposed within a recess-free portion of the hollow elongated body; and
wherein the first tendon and the second tendon are operably connected to the first joint, and the third tendon and the fourth tendon are operably connected to the second joint; wherein the guidewire tip has a width;
wherein a depth of each asymmetric recess of the first and second pluralities of asymmetric recesses is greater than 50% of the width of the guidewire tip;
wherein the routing wedge comprises wedge portions receivable through the slots; and
wherein the received wedge portions define a central channel and outer channels.

10. The guidewire tip of claim 9, wherein the hollow elongated body comprises a first end and an opposing second end;
wherein the first joint and the second joint are separated by a first length; and
wherein the first joint is separated from the second end by a second length.

11. The guidewire tip of claim 9, wherein the width of the guidewire tip is about 0.1 mm to about 0.9 mm.

12. The guidewire tip of claim 9, wherein the hollow elongated body comprises an internal wall;
wherein the first tendon and the second tendon are disposed on a first set of opposing sides of the internal wall; and
wherein the third tendon and the fourth tendon are disposed on a second set of opposing sides of the internal wall different from the first set of opposing sides.

13. The guidewire tip of claim 9, wherein the first tendon and the second tendon are attached to a distal end of the first joint; and
wherein the third tendon and the fourth tendon are attached to a distal end of the second joint.

14. The guidewire tip of claim 9, wherein the width of the guidewire tip is about 0.1 mm to about 0.9 mm;

wherein each of the tendons comprise a superelastic wire;
wherein the hollow elongated body comprises an internal wall;
wherein the first tendon and the second tendon are disposed on a first set of opposing sides of the internal wall;
wherein the third tendon and the fourth tendon are disposed on a second set of opposing sides of the internal wall different from the first set of opposing sides; wherein the first tendon and the second tendon are attached to a distal end of the first joint; wherein the third tendon and the fourth tendon are attached to a distal end of the second joint; and wherein the first and second pluralities of asymmetric recesses comprise grooves defined by substantially perpendicular walls.

15. The guidewire tip of claim 14, wherein the guidewire tip comprises biocompatible material.

16. The guidewire tip of claim 14, wherein the guidewire tip comprises nitinol.

17. The guidewire tip of claim 14, wherein the first plurality of asymmetric recesses is orthogonal to the second plurality of asymmetric recesses.

18. The guidewire tip of claim 9, wherein each asymmetric recess of the first and second pluralities of asymmetric recesses has a shape selected from a group consisting of rectangular, triangular, and sinusoidal.

19. The guidewire tip of claim 9 further comprising a control unit comprising:
a guidewire roller mechanism comprising a first roller and a second roller, and operably coupled to a first motor;
a guidewire actuation assembly comprising motors for advancing, retracting, and rotating the guidewire through the guidewire roller mechanism;
a groove path for storing the guidewire; and
a shaft operably coupled to an elastic coupling;
wherein the control unit is configured to cause:
the first joint to bend in a manner providing a first degree of freedom of movement; and
the second joint to bend in a manner providing a second degree of freedom of movement different from the first degree of freedom of movement;
wherein a portion of the guidewire is disposed between the first and second rollers; and
wherein the shaft is operable by a second motor and configured to unspool the guidewire from the groove path to the guidewire roller mechanism.

20. A robotically actuated system for steering a guidewire comprising:
an elongate hollow body comprising:
a first joint comprising a first set of asymmetric recesses in the elongate hollow body; and
a second joint comprising a second set of asymmetric recesses in the elongate hollow body;
a tendon system comprising tendons operably connected to the first joint and the second joints;
slots disposed within a recess-free portion of the elongate hollow body;
a routing wedge comprising wedge portions receivable through the slots and disposed fully within the elongate hollow body spatially separating the tendons from one another and defining a central channel and outer channels; and
a control unit operably connected to the tendon system;
wherein each of the tendons comprise a superelastic wire; and
wherein the control unit is configured to actuate the tendon system to cause:
the first joint to bend in a manner providing a first degree of freedom of movement; and
the second joint to bend in a manner providing a second degree of freedom of movement different from the first degree of freedom of movement.

21. The robotically actuated system of claim 20, wherein each asymmetric recess of the first and seconds sets of asymmetric recesses has a shape selected from a group consisting of rectangular, triangular, and sinusoidal.

22. The robotically actuated system of claim 20, wherein the control unit comprises:
a guidewire roller mechanism comprising a first roller and a second roller, and operably coupled to a first motor;
a guidewire actuation assembly comprising motors for advancing, retracting, and rotating the guidewire through the guidewire roller mechanism;
a groove path for storing the guidewire; and
a shaft operably coupled to an elastic coupling;
wherein a portion of the guidewire is disposed between the first and second rollers; and
wherein the shaft is operable by a second motor and configured to unspool the guidewire from the groove path to the guidewire roller mechanism.

* * * * *